(12) United States Patent
Domin et al.

(10) Patent No.: US 6,436,671 B1
(45) Date of Patent: Aug. 20, 2002

(54) LIPID KINASE

(75) Inventors: Jan Domin; Michael Derek Warerfield, both of London (GB)

(73) Assignee: Ludwig Institute for Cancer Research, Zurich (CH)

( * ) Notice: Subject to any disclaimer, the term of this patent is extended or adjusted under 35 U.S.C. 154(b) by 0 days.

(21) Appl. No.: 09/355,160

(22) PCT Filed: Jan. 27, 1998

(86) PCT No.: PCT/GB98/00244

§ 371 (c)(1),
(2), (4) Date: Oct. 1, 1999

(87) PCT Pub. No.: WO98/32864

PCT Pub. Date: Jul. 30, 1998

(30) Foreign Application Priority Data

Jan. 28, 1997 (GB) .............................................. 9701652

(51) Int. Cl.[7] .............................................. C12P 21/06
(52) U.S. Cl. ..................... 435/69.1; 435/70.1; 435/194; 435/320.1; 435/455; 536/23.5
(58) Field of Search ............................... 435/69.1, 70.1, 435/194, 320.1, 455; 530/350; 536/23.1, 23.5

(56) References Cited

U.S. PATENT DOCUMENTS 5,200,313 A * 4/1993 Carrico ......................... 435/6
5,948,664 A * 9/1999 Williams et al. ............. 435/194

OTHER PUBLICATIONS

Molz et al., Cpk Is a Novel Class of Drosophila PtdIns 3–Kinase Containing a C2 Domain, The Journal of Biological Chemistry vol. 217, No. 23, Jun. 7 1996, pp. 13892–13899.*

Volinia et al., A human phosphatisylinositaol 3–kinase complex related to the yeast Vps34p–Vps15p protein sorting system, The EMBO Journal vol. 14, No. 14, 1995, pp. 3339–3348.*

* cited by examiner

Primary Examiner—James Ketter
Assistant Examiner—Richard Schnizer
(74) Attorney, Agent, or Firm—Klauber & Jackson

(57) ABSTRACT

The invention relates to a novel human class II PI3-kinase and in particular the sequence of the isolated nucleic acid molecule and the encoded amino acid sequence. The novel human PI3-kinase is termed PI3K-C2α and has unique biochemical properties that characterize and distinguish it from known PI3-kinases. These include, amongst other things, resistance to the PI3-kinase inhibitors Wortmannin and LY294000, the lack of a p85 binding site, a divergent amino terminus and the absence of a polyproline motif which is typical of known type II PI3-kinases.

16 Claims, 16 Drawing Sheets

```
1/1                                      31/11
ATG GCT CAG ATA TTT AGC AAC AGC GGA TTT AAA GAA TGT CCA TTT TCA CAT CCG GAA CCA
 M   A   Q   I   F   S   N   S   G   F   K   E   C   P   F   S   H   P   E   P
61/21                                    91/31
ACA AGA GCA AAA GAT GTG GAC AAA GAA GAA GCA TTA CAG ATG GAA GCA GAG GCT TTA GCA
 T   R   A   K   D   V   D   K   E   E   A   L   Q   M   E   A   E   A   L   A
121/41                                   151/51
AAA CTG CAA AAG GAT AGA CAA GTG ACT GAC AAT CAG AGA GGC TTT GAG TTG TCA AGC AGC
 K   L   Q   K   D   R   Q   V   T   D   N   Q   R   G   F   E   L   S   S   S
181/61                                   211/71
ACC AGA AAA AAA GCA CAG GTT TAT AAC AAG CAG GAT TAT GAT CTC ATG GTG TTT CCT GAA
 T   R   K   K   A   Q   V   Y   N   K   Q   D   Y   D   L   M   V   F   P   E
241/81                                   271/91
TCA GAT TCC CAA AAA AGA GCA TTA GAT ATT GAT GTA GAA AAG CTC ACC CAA GCT GAA CTT
 S   D   S   Q   K   R   A   L   D   I   D   V   E   K   L   T   Q   A   E   L
310/101                                  331/111
GAG AAA CTA TTG CTG GAT GAC AGT TTC GAG ACT AAA AAA ACA CCT GTA TTA CCA GTT ACT
 E   K   L   L   L   D   D   S   F   E   T   K   K   T   P   V   L   P   V   T
361/121                                  391/131
CCT ATT CTG AGC CCT TCC TTT TCA GCA CAG CTC TAT TTT AGA CCT ACT ATT CAG AGA GGA
 P   I   L   S   P   S   F   S   A   Q   L   Y   F   R   P   T   I   Q   R   G
421/141                                  451/151
CAG TGG CCA CCT GGA TTA CCT GGG CCT TCC ACT TAT GCT TTA CCT TCT ATT TAT CCT TCT
 Q   W   P   P   G   L   P   G   P   S   T   Y   A   L   P   S   I   Y   P   S
481/161                                  511/171
ACT TAC AGT AAA CAG GCT GCA TTC CAA AAT GGC TTC AAT CCA AGA ATG CCC ACT TTT CCA
 T   Y   S   K   Q   A   A   F   Q   N   G   F   N   P   R   M   P   T   F   P
541/181                                  571/191
TCT ACA GAA CCT ATA TAT TTA AGT CTT CCG GGA CAA TCT CCA TAT TTC TCA TAT CCT TTG
 S   T   E   P   I   Y   L   S   L   P   G   Q   S   P   Y   F   S   Y   P   L
601/201                                  631/211
ACA CCT GCC ACA CCC TTT CAT CCA CAA GGA AGC TTA CCT ATC TAT CGT CCA GTA GTC AGT
 T   P   A   T   P   F   H   P   Q   G   S   L   P   I   Y   R   P   V   V   S
661/221                                  691/231
ACT GAC ATG GCA AAA CTA TTT GAC AAA ATA GCT AGT ACA TCA GAA TTT TTA AAA AAT GGG
 T   D   M   A   K   L   F   D   K   I   A   S   T   S   E   F   L   K   N   G
721/241                                  751/251
AAA GCA AGG ACT GAT TTG GAG ATA ACA GAT TCA AAA GTC AGC AAT CTA CAG GTA TCT CCA
 K   A   R   T   D   L   E   I   T   D   S   K   V   S   N   L   Q   V   S   P
781/261                                  811/271
AAG TCT GAG GAT ATC AGT AAA TTT GAC TGG TTA GAC TTG GAT CCT CTA AGT AAG CCT AAG
 K   S   E   D   I   S   K   F   D   W   L   D   L   D   P   L   S   K   P   K
841/281                                  871/291
GTG GAT AAT GTG GAG GTA TTA GAC CAT GAG GAA GAG AAA AAT GTT TCA AGT TTG CTA GCA
 V   D   N   V   E   V   L   D   H   E   E   E   K   N   V   S   S   L   L   A
901/301                                  931/311
AAG GAT CCT TGG GAT GCT GTT CTT CTT GAA GAG AGA TCG ACA GCA AAT TGT CAT CTT GAA
 K   D   P   W   D   A   V   L   L   E   E   R   S   T   A   N   C   H   L   E
961/321                                  991/331
AGA AAG GTG AAT GGA AAA TCC CTT TCT GTG GCA ACT GTT ACA AGA GCC AGT CTT TTA AAT
 R   K   V   N   G   K   S   L   S   V   A   T   V   T   R   S   Q   S   L   N
1021/341                                 1051/351
ATT CGA ACA ACT CAG CTT GCA AAA GCC CAG GGC CAT ATA TCT CAG AAA GAC CCA AAT GGG
 I   R   T   T   Q   L   A   K   A   Q   G   H   I   S   Q   K   D   P   N   G
1081/361                                 1111/371
ACC AGT AGT TTG CCA ACT GGA AGT TCT CTT CTT CAA GAA GTT GAA GTA CAG AAT GAG GAG
 T   S   S   L   P   T   G   S   S   L   L   Q   E   V   E   V   Q   N   E   E
1141/381                                 1171/391
ATG GCA GCT TTT TGT CGA TCC ATT ACA AAA TTG AAG ACC AAA TTT CCA TAT ACC AAT CAC
 M   A   A   F   C   R   S   I   T   K   L   K   T   K   F   P   Y   T   N   H
```

Fig. 1

```
1201/401                                    1231/411
CGC ACA AAC CCA GGC TAT TTG TTA AGT CCA GTC ACA GCG CAA AGA AAC ATA TGC GGA GAA
 R   T   N   P   G   Y   L   L   S   P   V   T   A   Q   R   N   I   C   G   E
1261/421                                    1291/431
AAT GCT AGT GTG AAG GTC TCC ATT GAC ATT GAA GGA TTT CAG CTA CCA GTT ACT TTT ACG
 N   A   S   V   K   V   S   I   D   I   E   G   F   Q   L   P   V   T   F   T
1321/441                                    1351/451
TGT GAT GTG AGT TCT ACT GTA GAA ATC ATT ATA ATG CAA GCC CTT TGC TGG GTA CAT GAT
 C   D   V   S   S   T   V   E   I   I   I   M   Q   A   L   C   W   V   H   D
1381/461                                    1411/471
GAC TTG AAT CAA GTA GAT GTT GGC AGC TAT GTT CTA AAA GTT TGT GGT CCA GAG GAA GTG
 D   L   N   Q   V   D   V   G   S   Y   V   L   K   V   C   G   Q   E   E   V
1441/481                                    1471/491
CTG CAG AAT AAT CAT TGC CTT GGA AGT CAT GAG CAT ATT CAA AAC TGT CGA AAA TGG GAC
 L   Q   N   N   H   C   L   G   S   H   E   H   I   Q   N   C   R   K   W   D
1501/501                                    1531/511
ACA GAA ATT AGA CTA CAA CTC TTG ACC TTC AGT GCA ATG TGT CAA AAT CTG GCC CGA ACA
 T   E   I   R   L   Q   L   L   T   F   S   A   M   C   Q   N   L   A   R   T
1561/521                                    1591/531
GCA GAA GAT GAT GAA ACA CCC GTG GAT TTA AAC AAA CAC CTG TAT CAA ATA GAA AAA CCT
 A   E   D   D   E   T   P   V   D   L   N   K   H   L   Y   Q   I   E   K   P
1621/541                                    1651/551
TGC AAA GAA GCC ATG ACG AGA CAC CCT GTT GAA GAA CTC TTA GAT TCT TAT CAC AAC CAA
 C   K   E   A   M   T   R   H   P   V   E   E   L   L   D   S   Y   H   N   Q
1681/561                                    1711/571
GTA GAA CTG GCT CTT CAA ATT GAA AAC CAA CAC CGA GCA GTA GAT CAA GTA ATT AAA GCT
 V   E   L   A   L   Q   I   E   N   Q   H   R   A   V   D   Q   V   I   K   A
1741/581                                    1771/591
GTA AGA AAA ATC TGT AGT GCT TTA GAT GGT GTC GAG ACT CTT GCC ATT ACA GAA TCA GTA
 V   R   K   I   C   S   A   L   D   G   V   E   T   L   A   I   T   E   S   V
1801/601                                    1831/611
AAG AAG CTA AAG AGA GCA GTT AAT CTT CCA AGG AGT AAA ACT GCT GAT GTG ACT TCT TTG
 K   K   L   K   R   A   V   N   L   P   R   S   K   T   A   D   V   T   S   L
1861/621                                    1891/631
TTT GGA GGA GAA GAC ACT AGC AGG AGT TCA ACT AGG GGC TCA CTT AAT CCT GAA AAT CCT
 F   G   G   E   D   T   S   R   S   S   T   R   G   S   L   N   P   E   N   P
1921/641                                    1951/651
GTT CAA GTA AGC ATA AAC CAA TTA ACT GCA GCA ATT TAT GAT CTT CTC AGA CTC CAT GCA
 V   Q   V   S   I   N   Q   L   T   A   A   I   Y   D   L   L   R   L   H   A
1981/661                                    2011/671
AAT TCT GGT AGG AGT CCT ACA GAC TGT GCC CAA AGT AGC AAG AGT GTC AAG GAA GCA TGG
 N   S   G   R   S   P   T   D   C   A   Q   S   S   K   S   V   K   E   A   W
2041/681                                    2071/691
ACT ACA ACA GAG CAG CTC CAG TTT ACT ATT TTT GCT GCT CAT GGA ATT TCA AGT AAT TGG
 T   T   T   E   Q   L   Q   F   T   I   F   A   A   H   G   I   S   S   N   W
2101/701                                    2131/711
GTA TCA AAT TAT GAA AAA TAC TAC TTG ATA TGT TCA CTG TCT CAC AAT GGA AAG GAT CTT
 V   S   N   Y   E   K   Y   Y   L   I   C   S   L   S   H   N   G   K   D   L
2161/721                                    2191/731
TTT AAA CCT ATT CAA TCA AAG AAG GTT GGC ACT TAC AAG AAT TTC TTC TAT CTT ATT AAA
 F   K   P   I   Q   S   K   K   V   G   T   Y   K   N   F   F   Y   L   I   K
2221/741                                    2251/751
TGG GAT GAA CTA ATC ATT TTT CCT ATC CAG ATA TCA CAA TTG CCA TTA GAA TCA GTT CTT
 W   D   E   L   I   I   F   P   I   Q   I   S   Q   L   P   L   E   S   V   L
2281/761                                    2311/771
CAC CTT ACT CTT TTT GGA ATT TTA AAT CAG AGC AGT GGA AGT TCC CCT GAT TCT AAT AAG
 H   L   T   L   F   G   I   L   N   Q   S   S   G   S   S   P   D   S   N   K
2341/781                                    2371/791
CAG AGA AAG GGA CCA GAA GCT TTG GGC AAA GTT TCT TTA CCT CTT TGT GAC TTT AGA CGG
 Q   R   K   G   P   E   A   L   G   K   V   S   L   P   L   C   D   F   R   R
2401/801                                    2431/811
TTT TTA ACA TGT GGA ACT AAA CTT CTA TAT CTT TGG ACT TCA TCA CAT ACA AAT TCT GTT
 F   L   T   C   G   T   K   L   L   Y   L   W   T   S   S   H   T   N   S   V
```

Fig. 1 continued

```
2461/821                                        2491/831
CCT GGA ACA GTT ACC AAA AAA GGA TAT GTC ATG GAA AGA ATA GTG CTA CAG GTT GAT TTT
 P   G   T   V   T   K   K   G   Y   V   M   E   R   I   V   L   Q   V   D   F
2521/841                                        2551/851
CCT TCT CCT GCA TTT GAT ATT ATT TAT ACA ACT CCT CAA GTT GAC AGA AGC ATT ATA CAG
 P   S   P   A   F   D   I   I   Y   T   T   P   Q   V   D   R   S   I   I   Q
2581/861                                        2611/871
CAA CAT AAC TTA GAA ACA CTA GAG AAT GAT ATA AAA GGG AAA CTT CTT GAT ATT CTT CAT
 Q   H   N   L   E   T   L   E   N   D   I   K   G   K   L   L   D   I   L   H
2641/881                                        2671/891
AAA GAC TCA TCA CTT GGA CTT TCT AAA GAA GAT AAA GCT TTT TTA TGG GAG AAA CGT TAT
 K   D   S   S   L   G   L   S   K   E   D   K   A   F   L   W   E   K   R   Y
2701/901                                        2731/911
TAT TGC TTC AAA CAC CCA AAT TGT CTT CCT AAA ATA TTA GCA AGC GCC CCA AAC TGG AAA
 Y   C   F   K   H   P   N   C   L   P   K   I   L   A   S   A   P   N   W   K
2761/921                                        2791/931
TGG GGT AAT CTT GCC AAA ACT TAC TCA TTG CTT CAC CAG TGG CCT GCA TTG TAC CCA CTA
 W   G   N   L   A   K   T   Y   S   L   L   H   Q   W   P   A   L   Y   P   L
2821/941                                        2851/951
ATT GCA TTG GAA CTT CTT GAT TCA AAA TTT GCT GAT CAG GAA GTA AGA TCC CTA GCT GTG
 I   A   L   E   L   L   D   S   K   F   A   D   Q   E   V   R   S   L   A   V
2881/961                                        2911/971
ACC TGG ATT GAG GCC ATT AGT GAT GAT GAG CTA ACA GAT CTT CTT CCA CAG TTT GTA CAA
 T   W   I   E   A   I   S   D   D   E   L   T   D   L   L   P   Q   F   V   Q
2941/981                                        2971/991
GCT TTG AAA TAT GAA ATT TAC TTG AAT AGT TCA TTA GTG CAA TTC CTT TTG TCC AGG GCA
 A   L   K   Y   E   I   Y   L   N   S   S   L   V   Q   F   L   L   S   R   A
3001/1001                                       3031/1011
TTG GGA AAT ATC CAG ATA GCA CAC AAT TTA TAT TGG CTT CTC AAA GAT GCC CTG CAT GAT
 L   G   N   I   Q   I   A   H   N   L   Y   W   L   L   K   D   A   L   H   D
3061/1021                                       3091/1031
GTA CAG TTT AGT ACC CGA TAC GAA CAT GTT TTG GGT GCT CTC CTG TCA GTA GGA GGA AAA
 V   Q   F   S   T   R   Y   E   H   V   L   G   A   L   L   S   V   G   G   K
3121/1041                                       3151/1051
CGA CTT AGA GAA GAA CTT CTA AAA CAG ACG AAA CTT GTA CAG CTT TTA GGA GGA GTA GCA
 R   L   R   E   E   L   L   K   Q   T   K   L   V   Q   L   L   G   G   V   A
3181/1061                                       3211/1071
GAA AAA GTA ACG CAG GCT AGT GGA TCA GCC AGA CAG GTT GTT CTC CAA AGA AGT ATG GAA
 E   K   V   R   Q   A   S   G   S   A   R   Q   V   V   L   Q   R   S   M   E
3241/1081                                       3271/1091
CGA GTA CAG TCC TTT TTT CAG AAA AAT AAA TGC CTG CTC CCT CTC AAG CCA AGT CTA GTG
 R   V   Q   S   F   F   Q   K   N   K   C   L   P   L   K   P   S   L   V
3301/1101                                       3331/1111
GCA AAA GAA TTA AAT ATT AAG TCG TGT TCC TTC TTC AGT TCT AAT GCT GTC CCC CTA AAA
 A   K   E   L   N   I   K   S   C   S   F   F   S   S   N   A   V   P   L   K
3361/1121                                       3391/1131
GTC ACA ATG GTG AAT GCT GAC CCT CTG GGA GAA GAA ATT AAT GTC ATG TTT AAG GTT GGT
 V   T   M   V   N   A   D   P   L   G   E   E   I   N   V   M   F   K   V   G
3421/1141                                       3451/1151
GAA GAT CTT CGG CAA GAT ATG TTA GCT TTA CAG ATG ATA AAG ATT ATG GAT AAG ATC TGG
 E   D   L   R   Q   D   M   L   A   L   Q   M   I   K   I   M   D   K   T   W
3481/1161                                       3511/1171
CTT AAA GAA GGA CTA GAT CTG AGG ATG GTA ATT TTC AAA TGT CTC TCA ACT GGC AGA GAT
 L   K   E   G   L   D   L   R   M   V   I   F   K   C   L   S   T   G   R   D
3541/1181                                       3571/1191
CGA GGC ATG GTG GAG CTG GTT CCT GCT TCC GAT ACC CTC AGG AAA ATC CAA CTG GAA TAT
 R   G   M   V   E   L   V   P   A   S   D   T   L   R   K   I   Q   V   E   Y
3601/1201                                       3631/1211
GGT GTG ACA GGA TCC TTT AAA GAT AAA CCA CTT GCA GAG TGG CTA AGG AAA TAC AAT CCC
 G   V   T   G   S   F   K   D   K   P   L   A   E   W   L   R   K   Y   N   P
3661/1221                                       3691/1231
TCT GAA GAA GAA TAT GAA AAG GCT TCA GAG AAC TTT ATC TAT TCC TGT GTC GGA TGC TGT
 S   E   E   E   Y   E   K   A   S   E   N   F   I   Y   S   C   A   G   C   C
```

Fig. 1 continued

```
3721/1241                           3751/1251
GTA GCC ACC TAT GTT TTA GGC ATC TGT GAT CGA CAC AAT GAC AAT ATA ATG CTT CGA AGC
 V   A   T   Y   V   L   G   I   C   D   R   H   N   D   N   I   M   L   R   S
3781/1261                           3811/1271
ACG GGA CAC ATG TTT CAC ATT GAC TTT GGA AAG TTT TTG GGA CAT GCA CAG ATG TTT GGC
 T   G   H   M   F   H   I   D   F   G   K   F   L   G   H   A   Q   M   F   G
3841/1281                           3871/1291
AGC TTC AAA AGG GAT CGG GCT CCT TTT GTG CTG ACC TCT GAT ATG GCA TAT GTC ATT AAT
 S   F   K   R   D   R   A   P   F   V   L   T   S   D   M   A   Y   V   I   N
3901/1301                           3931/1311
GGG GGT GAA AAG CCC ACC ATT CGT TTT CAG TTG TTT GTG GAC CTC TGC TGT CAG GCC TAC
 G   G   E   K   P   T   I   R   F   Q   L   F   V   D   L   C   C   Q   A   Y
3961/1321                           3991/1331
AAC TTG ATA AGA AAG CAG ACA AAC CTT TTT CTT AAC CTC CTT TCA CTG ATG ATT CCT TCA
 N   L   I   R   K   Q   T   N   L   F   L   N   L   L   S   L   M   I   P   S
4021/1341                           4051/1351
GGG TTA CCA GAA CTT ACA AGT ATT CAA GAT TTG AAA TAC GTT AGA GAT GCA CTT CAA CCC
 G   L   P   E   L   T   S   I   Q   D   L   K   Y   V   R   D   A   L   Q   P
4081/1361                           4111/1371
CAA ACT ACA GAC GCA GAA GCT ACA ATT TTC TTT ACT AGG CTT ATT GAA TCA AGT TTG GGA
 Q   T   T   D   A   E   A   T   I   F   F   T   R   L   I   E   S   S   L   G
4141/1381                           4171/1391
AGC ATT GCC ACA AAG TTT AAC TTC TTC ATT CAC AAC CTT GCT CAG CTT CGT TTT TCT GGT
 S   I   A   T   K   F   N   F   F   I   H   N   L   A   Q   L   R   F   S   G
4201/1401                           4231/1411
CTT CCT TCT AAT GAT GAG CCC ATC CTT TCA TTT TCA CCT AAA ACA TAC TCC TTT AGA CAA
 L   P   S   N   D   E   P   I   L   S   F   S   P   K   T   Y   S   F   R   Q
4261/1421                           4291/1431
GAT GGT CGA ATC AAG GAA GTC TCT GTT TTT ACA TAT CAT AAG AAA TAC AAC CCA GAT AAA
 D   G   R   I   K   E   V   S   V   F   T   Y   H   K   K   Y   N   P   D   K
4321/1441                           4351/1451
CAT TAT ATT TAT GTA GTC CGA ATT TTG TGG GAA GGA CAG ATT GAA CCA TCA TTT GTC TTC
 H   Y   I   Y   V   V   R   I   L   W   E   G   Q   I   E   P   S   F   V   F
4381/1461                           4411/1471
CGA ACA TTT GTC GAA TTT CAG GAA CTT CAC AAT AAG CTC AGT ATT ATT TTT CCA CTT TGG
 R   T   F   V   E   F   Q   E   L   H   N   K   L   S   I   I   F   P   L   W
4441/1481                           4471/1491
AAG TTA CCA GGC TTT CCT AAT AGG ATG GTT CTA GGA AGA ACA CAC ATA AAA GAT GTA GCA
 K   L   P   G   F   P   N   R   M   V   L   G   R   T   H   I   K   D   V   A
4501/1501                           4531/1511
GCC AAA AGG AAA ATT GAG TTA AAC AGT TAC TTA CAG AGT TTG ATG AAT GCT TCA ACG GAT
 A   K   R   K   I   E   L   N   S   Y   L   Q   S   L   M   N   A   S   T   D
4561/1521                           4591/1531
GTA GCA GAG TGT GAT CTT GTT TGT ACT TTC TTC CAC CCT TTA CTT CGT GAT GAG AAA GCT
 V   A   E   C   D   L   V   C   T   F   F   H   P   L   L   R   D   E   K   A
4621/1541                           4651/1551
GAA GGG ATA GCT AGG TCT GCA GAT GCA GGT TCC TTC AGT CCT ACT CCA GGC CAA ATA GGA
 E   G   I   A   R   S   A   D   A   G   S   F   S   P   T   P   G   Q   I   G
4681/1561                           4711/1571
GGA GCT GTG AAA TTA TCC ATC TCT TAC CGA AAT GGT ACT CTT TTC ATC ATG GTG ATG CAT
 G   A   V   K   L   S   I   S   Y   R   N   G   T   L   F   I   M   V   M   H
4741/1581                           4771/1591
ATC AAA GAT CTT GTT ACT GAA GAT GGA GCT GAC CCA AAT CCA TAT GTC AAA ACA TAC CTA
 I   K   D   L   V   T   E   D   G   A   D   P   N   P   Y   V   K   T   Y   L
4801/1601                           4831/1611
CTT CCA GAT AAC CAC AAA ACA TCC AAA CGT AAA ACC AAA ATT TCA CGA AAA ACG AGG AAT
 L   P   D   N   H   K   T   S   K   R   K   T   K   I   S   R   K   T   R   N
4861/1621                           4891/1631
CCG ACA TTC AAT GAA ATG CTT GTA TAC AGT GGA TAT AGC AAA GAA ACC TAA GAC AGC GA
 P   T   F   N   E   M   L   V   Y   S   G   Y   S   K   E   T   L   R   Q   R
4921/1641                           4951/1651
GAA CTT CAA CTA AGT GTA CTC AGT GCA GAA TCT CTG CGG GAG AAT TTT TTC TTG GGT GGA
 E   L   Q   L   S   V   L   S   A   E   S   L   R   E   N   F   F   L   G   G
```

*Fig. 1 continued*

```
4981/1661                              5011/1671
GTA ACC CTG CCT TTG AAA GAT TTC AAC TTG AGC AAA GAG ACG GTT AAA TGG TAT CAG CTG
 V   T   L   P   L   K   D   F   N   L   S   K   E   T   V   K   W   Y   Q   L
5041/1681
ACT GCG GCA ACA TAC TTG TAA
 T   A   A   T   Y   L   *
```

Cos 7

N-term glu tag
PI3K-C2α

LIPID KINASE

The invention relates to a novel class II PI3 kinase, termed PI3K-C2α, and in particular the isolation thereof having regard to its relevant sequence structure and/or biochemical characteristics; means used in the isolation or production thereof; antibodies adapted to bind thereto; and assay kits relating thereto.

Phosphoinositides have been implicated in a variety of cellular processes as diverse as vacuolar protein sorting (1,2), cytoskeletal remodelling (3) and mediating intracellular signalling events through which growth factors, hormones and neurotransmitters exert their physiological effects on cellular activity, proliferation and differentiation (4,5,6).

Recently a family of proteins have been cloned and characterised and shown to be enzymes catalysing the addition of phosphate to inositol. Eukaryotic cells contain a variety of inositol derivatives phosphorylated to different extents. PtdIns(3)P is constitutively present in eukaryotic cells and its levels are constant upon extracellular stimulation. PtdIns(3,4)$P_2$ and PtdIns(3,4,5)$P_3$ (7,8) are virtually absent in resting cells but are rapidly induced upon stimulation with a variety of ligands. The enzymes catalysing these reactions are phosphoinositide lipid kinases (hereinafter called PI3 kinases). A brief overview of the current data in relation to PI3 kinases classifies these enzymes into three distinct groups being designated to an individual class by their in vitro substrate specificity, biochemical characteristics and, in examples where a definitive function has been assigned, the nature of the biochemical activity regulated by the specific kinase.

PI3 kinase class 1 polypeptides have a broad spectrum activity, phosphorylating inositol lipids PtdIns, PtdIns(4)P and PtdIns(4, 5)$P_2$. Class I kinases are subdivided into Class IA and IB. Class IA polypeptides include p110α (9), p110β (10) and p110δ (11) which interact physically with the adaptor sub-unit protein p85. Moreover, p110α and p100 have a broad distribution in terms of expression pattern. p110δ expression seems to be restricted to white blood cells. Class 1B includes p110γ (12) which functions independently of p85. Although each of these Class 1 kinases catalyse phosphate addition to inositol lipid, the mechanism via which these enzymes are activated and regulated is achieved by different molecular mechanisms.

Class II PI3 kinases have a restricted substrate specificity phosphorylating PtdIns and PtdIns(4)P but not PtdIns(4,5) $P_2$. Each of the kinases of this class are characterised by a conserved C2 domain in the carboxyl terminal region of the protein. The presence of conserved motifs within the C2 domain indicates that this region may confer regulation via calcium and/or phospholipid. A comparison of the murine and Drosophila class II kinases mp170 and PI3K_68D respectively reveals a high degree of homology in the kinase domain of these proteins. Significant divergence occurs at the amino terminal regions of these polypeptides suggesting that adaptor proteins interacting with these variable domains may regulate kinase activity. Class II PI3 kinases do not interact with p85.

The third class of PI3 kinase, class III PI3 Kinase, is related to the S.cerevisiae gene Vps34 (1). This kinase was originally isolated as a gene involved in regulating vesicle mediated membrane-trafficking in yeast. The human homologue of Vps34 is complexed with a ser/thr kinase called Vps15p (14,15). Of the three classes of PI3 kinase this has the most restricted substrate specificity being strictly limited to PtdIns.

A novel human class II PI3 kinase is herein described and termed human PI3K-C2α. It is characterised as a class II kinase due to the presence of a conserved C2 domain found in murine and Drosophila class II PI3 kinases (FIG. 2), its apparent lack of a p85 binding site and a substrate specificity limited to PtdIns and PtdIns (4) P (FIG. 4). The polypeptide is unique in that this is the first human class II kinase to be described. It has significant divergence in the amino terminal region of the protein when compared to the mouse homologue of human PI3K-C2α (16). It is also, surprisingly, the first PI3 kinase to be isolated that has resistance to PI3 kinase inhibitors Wortmannin and LY294002 (FIG. 5).

The use of selected inhibitors has proved extremely useful in analysing intracellular signal transduction cascades. Inhibitors used at low concentrations probably result in the modification of a single protein's function thereby allowing the dissection of signal transduction pathways. A good example of this is the use of Pertussis toxin which is a cell permeant agent (17). The agent undergoes endocytosis into intact cells and results in the ADP-ribosylation of specific GTP-binding or G-proteins. This modification uncouples these G-proteins from their receptors therefore interfering with the cell's response to receptor stimuli. Wortnannin is another cell permeant inhibitor (18,19). It is a fungal metabolite and has been shown to have in vivo anti-inflammatory or immunosuppressive effects in animal models. Wortmannin was first shown to inhibit cellular responses to receptor stimulation in neutrophils. The drug inhibited the respiratory burst induced by ligands such as N-formyl-Met-Leu-Phe, (fMLP),C5a,leukotriene B4 or platelet-activating factors. Importantly, Wortmannin failed to inhibit cellular response to TPA suggesting differential responses to the drug. In particular, the fact that the stimulation of calcium mobilising receptors is resistant to Wortnannin suggests that intracellular signalling initiated by these receptors is controlled by a quite separate kinase cascade.

The identification of PI3 kinases as the target for Wortmannin came from in vitro metabolic labelling of guinea pig neutrophils with $^{32}$P to monitor the uptake of phosphate into phospholipids in the presence of specific kinase inhibitors (20). In control experiments stimulation of fMLP receptors resulted in $^{32}$P labelling of phosphatidic acid and PtdIns(3, 4,5)$P_3$. The presence of Pertussis toxin had no effect on the phosphorylation of these phospholipids. However, pre-incubation of leucocytes with Wortmannin resulted in inhibition of $^{32}$P incorporation into only PtdIns(3,4,5)$P_3$. Since this is the product of PI3 kinase catalysed reactions it seems likely that Wortnannin was specifically targeting PI3 kinase. Subsequently, Wortmannin has been shown to block a number of physiological processes including many insulin stimulated actions that would result in enhanced glucose utilisation (21). Wortnannin has proved to be an effective inhibitor of mammalian PI3 kinases. To date, no human PI3 kinase has been cloned and shown to be resistant to this agent.

The isolation and sequencing of an as yet unidentified human PI3 kinase that has significant homology to previously identified murine and Drosophila class II kinases is described (16,22,23). Comparison of the optimal alignment of these aforementioned proteins shows the human protein to be 32.5% homologous with sequences of the Drosophila PI3K_68D and cpk proteins and 90.8% and 90.2% with the murine proteins mp170 and mcpk, FIG. 2. The carboxyl terminal region of the aforementioned proteins have increased homology due to the presence of a conserved C2 domain. This domain is characterised by the presence of motifs likely to be involved in the modulation of kinase activity by calcium and/or phospholipid.

The amino terminal region of human PI3K-C2α is extended by 176 amino acid residues which are lacking in the murine sequence of mp170. The murine mcpk protein has a 28 amino acid residue deletion in this region that is absent from human PI3K-C2α and a mp170. This divergence in sequence may be explained by the presence of the unique binding sites for adaptor proteins that regulate kinase activity. This is supported by the lack of an apparent p85 binding motif.

Furthermore, immunofluoresence experiments using a monoclonal antibody to the amino terminal glu-tag of PI3K-C2α reveals a punctate cytoplasmic distribution in Cos cells expressing the recombinant glu-tagged PI3K-C2α protein, FIG. 9. Moreover subcellular fractionation of Monkey Kidney Cos cells shows that epitope tagged PI3K-C2α is tightly associated with phospholipid containing membranes. The nature of this interaction is currently unknown but may be mediated via phospholipid interaction with the C2 domain or alternatively through binding to an additional polypeptide localised to microsomes and plasma membranes.

The recombinantly produced PI3K-2Cα kinase shows increased resistance to the general PI3 kinase inhibitors Wortmannin and LY294002, (FIG. 5) To date, all cloned human PI3 kinases have been found to be sensitive to these inhibitors. Studies of the Wortmannin sensitive class I PI3 kinase p110α identifies residue lys-802 as being the site of Wortmannin covalent inactivation of kinase activity, a residue near or at the active site and involved in phosphate transfer. This residue is present in all PI3 kinase family members and also in PI3K-2Cα, therefore the resistance to Wortmannin by PI3K-2Cα is not apparent.

Additionally it will be apparent that alternate methods for use in modulating the activity of PI3K-2Cα exists.

For example, having regard to the sequence data provided herein it is possible to provide antisense material which prevents the expression of PI3K-2Cα.

As mentioned above, the invention embraces antisense oligonucleotides that selectively bind to a nucleic acid molecule encoding a PI3K-2Cα protein, to decrease transcription and/or translation of PI3K-2Cα genes. This is desirable in virtually any medical condition wherein a reduction in PI3K-2Cα gene product expression is desirable, including to reduce any aspect of a tumor cell phenotype attributable to PI3K-2Cα gene expression. Antisense molecules, in this manner, can be used to slow down or arrest such aspects of a tumor cell phenotype.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and thereby, inhibits the transcription of that gene and/or the translation of that mRNA. The antisense molecules are designed so as to interfere with transcription or translation of a target gene upon hybridization with the target gene. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon the DNA sequence presented in FIG. 1 or upon allelic or homologous genomic and/or DNA sequences, one of skill in the art can easily choose and synthesize any of a number of appropriate antisense molecules for use in accordance with the present invention. In order to be sufficiently selective and potent for inhibition, such antisense oligonucleotides should comprise at least 7 (Wagner et al., Nature Biotechnology 14:840–844, 1996) and, more preferably, at least 15 consecutive bases which are complementary to the target. Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., Cell Mol. Neurobiol. 14(5):439–457, 1994) and at which proteins are not expected to bind. Finally, although FIG. 1 discloses cDNA sequence, one of ordinary skill in the art may easily derive the genomic DNA corresponding to the cDNA of FIG. 1. Thus, the present invention also provides for antisense oligonucleotides which are complementary to the genomic DNA corresponding to FIG. 1. Similarly, antisense to allelic or homologous DNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness. The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, phosphate triesters, acetamidates, peptides, and carboxymethyl esters.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-0-alkylated ribose group. In addition, modified oligonucleotides may include sugars such as arabinose instead of ribose. Modified oligonucleotides also can include base analogs such as C-5 propyne modified bases (Wagner et al., Nature Biotechnology 14:840–844, 1996). The present invention, thus, contemplates pharmaceutical preparations containing modified antisense molecules that are complementary to and hybridizable with, under physiological conditions, nucleic acids encoding PI3K-C2α proteins, together with pharmaceutically acceptable carriers.

Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

It follows from the foregoing description that it is an object of this invention to isolate the nucleic acid sequence and derived amino acid sequence of the first human class II PI3 kinase.

It is a further object of this invention to recombinantly manufacture human PI3K-C2α kinase.

It is a further object of this invention to use computer assisted three dimensional reconstruction of human PI3K-C2α kinase protein to facilitate the identification of agonists or antagonists of PI3K-C2α.

It is a yet further object to use said three dimensional reconstruction to design ligands that may modulate the biochemical activity of human PI3-C2αkinase.

It is yet a further object of this invention to manufacture an antibody, preferably monoclonal, to PI3K-C2α, and more preferably further still to manufacture a humanised antibody to PI3K-C2α.

It is yet a further object of this invention that the monoclonal antibody be specific to class II PI3 kinases.

It is yet a further object of this invention to provide an assay kit for use in identifying said protein.

According to the first aspect of the invention there is provided the isolated nucleic acid molecule and/or corresponding protein of human PI3K-C2α as shown in FIG. 1, including any deletions, additions or substitutions, or a complementary sequence thereto.

In a preferred embodiment of the invention said complementary sequence binds to said nucleic acid sequence under stringent conditions. Preferably, these conditions include 0.5M sodium phosphate, pH7.2, 7% SDS, 1 mM EDTA at 65° C.

In yet a further preferred embodiment of the invention said deletions, additions or substitutions do not alter the function of the protein or indeed do not alter the function in a deleterious manner thus, in one example, a nucleic acid molecule may be provided that binds to the relevant gene to prevent expression of P13K-C2α.

In yet a further preferred embodiment of the invention said deletions, additions or substitutions do alter the function of the protein. Thus, in one example, a mutation in PI3K-C2α could produce a dominant negative mutation that results in the inactivation of endogenous P13K-C2α in transfected or transformed cells.

According to a second aspect of the invention there is provided an antibody, or at least an effective part thereof, which binds at least with a selective part of said human PI3K-C2α.

Ideally said effective part comprises FAb fragments.

Ideally said antibody is polyclonal or monoclonal and ideally farther still said antibody is specific to class II PI3 Kinases. Ideally said antibody is humanised by recombinant methods to contain the variable region of said antibody with an invariant or constant region of a human antibody.

Ideally said antibody is provided with a marker including a conventional label or tag, for example a radioactive and/or fluorescent and/or epitope label or tag.

More ideally still said humanised monoclonal antibody to class II PI3-kinases is produced as a fusion polypeptide in an expression vector suitably adapted for transfection or transformation of prokaryotic or eukaryotic cells.

According to a yet further aspect of the invention there is provided a construct including all, or part of, the said nucleic acid molecule of the invention.

In a preferred embodiment of the invention said construct is adapted to be a cloning vehicle for human PI3K-C2α.

In a preferred embodiment of the invention said cloning vehicle may be used for expression of the protein sequence of human PI3K-C2α in transformed or transfected prokaryotic and eukaryotic cells. Preferably said cloning vehicle is adapted for use in E.coli, mammalian, insect, amphibian or fungal cells.

In a preferred embodiment of the invention said construct includes nucleic acid encoding at least a part of human PI3K-C2α which is functionally linked to a promoter so as to provide for either constitutive or inducible expression of human PI3K-C2α kinase. Preferably further still said construct is adapted for cell/tissue specific expression of PI3K-C2α.

According to a yet further aspect of the invention there is provided cells transformed or transfected with the cloning vehicle of the invention and so including the nucleic acid sequence molecule encoding human PI3K-C2α or a part thereof.

According to a yet further aspect of the invention there is provided recombinantly manufactured human PI3K-C2α.

According to a yet further aspect of the invention there is provided human PI3K-C2α kinases or a fraction thereof, which is characterised by insensitivity to the PI3 kinase(s) inhibitor Wortmannin and/or LY294002.

In a further preferred embodiment of this aspect of the invention said protein is also, or alternatively, characterised by the absence of a p85 binding site. In a further preferred embodiment of this aspect of the invention said protein is also, or alternatively, characterised by the absence of a type II polyproline motif present in Drosophilia P13K__68D and cpk.

In a yet a further preferred embodiment of this aspect of the invention said protein is also, or alternatively, characterised by divergent amino terminal region when compared to other class II PI3 kinases.

In a yet a further preferred embodiment of this aspect of the invention said protein is characterised by a molecular weight of 190 Kda.

In yet a further preferred embodiment of this aspect of the invention said protein is also, or alternatively, characterised by an in vitro substrate specificity that is restricted to PtdIns, PtdIns(4)P or at least PtdIns, PtdIns(4)P.

In any of the above embodiments of the invention said fraction ideally comprises the full length amino acid sequence or truncations thereof.

According to a further aspect of the invention there is provided the isolated genomic DNA and/or cDNA of human PI3K-C2α kinase according to any previous aspect of the invention.

According to a yet further aspect of the invention there is provided a process for the isolation of human PI3K-C2α kinase which process includes a PCR reaction.

In a preferred process of the invention said PCR reaction comprises use of at least two primers adapted to bind to at least one selected part of nucleic acid of human PI3K-C2α; and further said process also comprises the provision of conditions for amplifying at least one selected part of said nucleic acid using said primers; and further, following amplification, said process comprises the purification of the amplified product(s); and, optionally, isolation of at least one amplified fragment.

In a preferred process of the invention said primers are designed to selectively bind to the nucleic acid of class II kinases and ideally class II human kinases.

In yet a further preferred embodiment of the invention said primers are as follows:
sense 5'GGNGA T/C GA T/C T/C T A/G CGNCA A/G GA3' (SEQ ID NO:4)
antisense 5'A/G AA A/G TGICC A/G AA A/G TC AIGIT AT A/G TG A/G TG A/G AA3' (SEQ ID NO:5)

In yet a further preferred embodiment of the invention said primers include any one or more deletions, additions or substitutions which do not deleteriously affect the functional effectiveness of the primers.

According to a yet further aspect of the invention there is provided the use of any one of more of the aforementioned primers to isolate class II PI3 kinases and ideally human PI3K-C2α.

According to a yet further aspect of the invention there is provided the use of any one or more of the aforementioned primers to isolate human PI3 kinases and ideally human PI3K-C2α.

According to a yet further aspect of the invention there is provided an agent which is adapted to interact with the amino terminal region, or any part thereof, of human PI3K-C2α kinase.

According to a yet further aspect of the invention there is provided an assay kit for identifying human PI3K-C2α either intracellularly or in a cellular extract.

In a preferred embodiment of the invention said assay kit is a diagnostic kit.

Preferably said assay kit, or said diagnostic kit makes use of any one or more of the following techniques: western blotting; immunoprecipitation; immunofluorescence on whole cells or tissue sections; or quantitative ELISA reactions.

According to a yet further aspect of the invention there is provided a method for identifying agonists or antagonists effective at enhancing or blocking the activity of the polypeptide of the invention which comprises screening candidate molecules for such activity using the polypeptide, or fragments thereof the invention.

Ideally, screening may involve artificial techniques such as computer-aided techniques or conventional laboratory techniques.

Alternatively, the method of the invention may involve competitive binding assays in order to identify agents that selectively and ideally irreversibly bind to the polypeptide of the invention.

According to a yet further aspect of the invention there is provided a pharmaceutical or veterinary composition comprising an agent effective at enhancing or blocking the activity of the polypeptide of the invention which has been formulated for pharmaceutical or veterinary use and which optionally also includes a dilutant, carrier or excipient and/or is in unit dosage form.

According to a yet further aspect of the invention there is provided antisense oligonucleotide or a modified antisense oligonucleotide as herein described adapted to hybridise to at least part of the nucleic acid molecule shown in FIG. 1.

Thus, in general terms the invention describes the nucleic acid sequence and derived amino acid sequence of a novel human class II PI3 kinase, human PI3K-C2α, which has novel features in relation to sequence, biochemistry and responses to well characterised inhibitors of PI3 kinases.

An embodiment of the invention will now be described, by example only, and with reference to the following figures, materials and methods wherein;

FIG. 1 represents the complete cDNA sequence (SEQ ID NO:1) and amino acid sequence (SEQ ID NO:2) of PI3K-C2α;

MATERIALS AND METHODS

Identification of PI3K-C2α cDNA

Figure 2A:
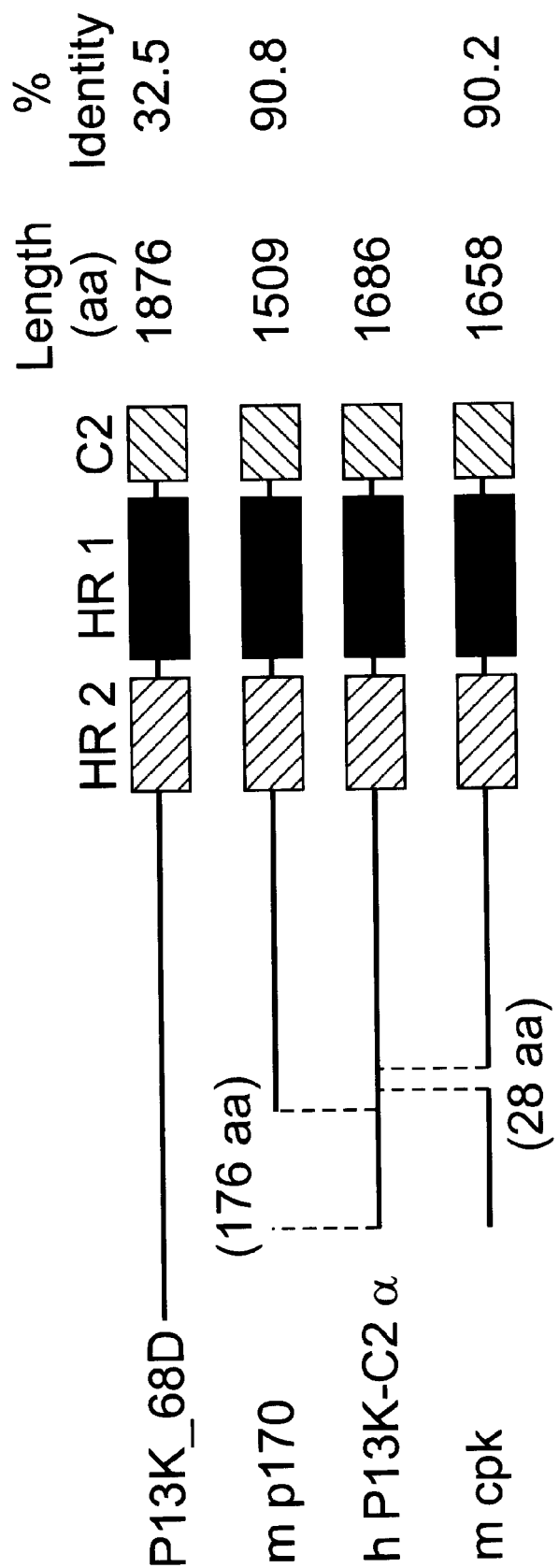
FIG. 2 shows a comparison of the conserved domains found in type II PI3 kinases (SEQ ID NOs:2, 7, and 8) and in particular the kinase domains and C2-domains.

Poly A+RNA was isolated from U937 cells using oligo (dT) cellulose (Stratagene) and used to synthesise first strand cDNA with AMV reverse transcriptase (Pharmacia). PCR reactions were then performed using Taq DNA polymerase (Life Technologies), first strand cDNA, 4 mM Mg2+ and 1 μM primers. The nucleotide sequences of the primers used were sense—GGNGA T/C GA T/C T/CT A/G CGNCA A/G GA (SEQ ID NO:4) (GDDLRQD/E) (SEQ ID NO:9) and antisense—A/G AA A/G TGICC A/G AA A/G TC A/G/T AT A/G TG A/G TG A/G AA (SEQ ID NO:5) (GHIDFGHF) (SEQ ID NO:10). To facilitate subsequent cloning, an EcoRI restriction site was incorporated into the 5' end of each primer. The conditions used were 30 cycles of 94° C. for 30 s, 56° C. for 30 s, and 72° C. for 30 s. After sub cloning into a Bluescript-SK vector, individual clones were selected and sequenced (ABI).

Isolation of PI3K-C2α cDNA

The PCR fragment was excised from the vector, labelled with $^{32}$P dCTP using random primers (Amersham) and used to screen a 1λzap U937 cDNA library (Stratagene). Approximately $3\times10^6$ plaques were plated and transferred onto Hybond-N filters (Amersham). These were hybridised with the probe for 16 hours at 65° C. in 0.5M sodium phosphate pH7.2, 7% SDS and imM EDTA. After this time, the filters were washed twice with 0.5×SSC/0.1% SDS for 20 minutes at 60° C. and positive clones identified by autoradiography. After three rounds of screening, clones were plaque purified and the cDNA insert in Bluescript-SK was rescued using ExAssist helper phage (Stratagene). The nucleotide sequence of the longest clone was determined using both Taq di deoxy terminator cycle sequencing (ABI) and di deoxy chain termination using T7 DNA polymerase and a $^{35}S$ thio dATP (Lark Sequencing Technologies).

The 5' end of the Cdna was obtained by rapid amplification of cDNA ends. cDNA was synthesised (Life Technologies) using primers complementary to the original cDNA sequence (CTCTTCCTCATGGTCTAATACCTCCAC (SEQ ID NO:3) and TATCTCCAAATCAGTCCTTGCTTTCCC) (SEQ ID NO:6) from poly A+mRNA obtained from U937 cells. After sequencing, this fragment was ligated onto the parent cDNA in a pBK-CMV vector (Stratagene) to produce the full length PI3K-C2α cDNA.

Northern Blot Analysis

Multiple human tissue poly A+mRNA blots (Clontech) were hybridised with a 1.46 kb cDNA fragment corresponding to nucleotides 789–2249 of the PI3K-2α coding sequence. The probe was labelled using $[\alpha^{32}P]$ dCTP and random rimers (Amersham). Hybridizations were performed in EXPRESS HYB (Clontech) at 65° C. for 16 hours. The blots were washed twice with 2×SSC, 0.05% SDS at room temperature and twice in 1×SSC, 0.1% SDS at 50° C. Bands were visualised by autoradiography.

Plasmid Constructs and Expression of Recombinant Protein in Sf9 cells

PI3K-C2α cDNA corresponding to amino acid residues 148–1686 was ligated in the pAcGex vector (44). Recombinant DNA (2µg) was transfected into Sf9 cells with 0.25µg BACULOGOLD DNA (Pharmingen) using LIPOFECTIN (Gibco). Infections and amplifications (6×10$^5$ cells/ml) of the viral stocks were performed for 48–60 hours or 96 hours respectively (45). After protein expression, cells were harvested and lysed in 10 mM Tris/HCl (pH7.6), 5 mM EDTA, 50 mM NaCl, 30 mM sodium pyrophosphate, 50 mM NaF, 100 µM Na$_3$VO$_4$, 1% TRITON X-100 and 1 mM phenyl-methysulphonyl fluoride (lysis buffer). The extracts were incubated with glutathione-Sepharose beads (Pharmacia) for 2–4 hours at 4° C. Bound proteins were recovered by centrifugation and after repeated washing with lysis buffer, the protein was transferred to storage buffer (50% ethyleneglycol, 5 mM EDTA, 40 mM Tris-HCl pH7.4, 5 mM dithiothriotol, 10 mM benzamidine) at −20° C.

Generation of Antisera to PI3K-C2α

An amino-tenninal fragment of the PI3K-C2α cDNA (1–110 bp) was subcloned into pGex-2T vector. This plasmid was used to transform bacteria and the expression of a glutathione S-transferase (GST) fusion protein was induced. This protein was isolated using glutathione-sepharose beads and then eluted upon addition of excess glutathione. The GST fusion protein was used to immunise two rabbits, one of which produced antisera suitable for immunoprecipitation and western blotting PI3K-C2α from cell lysates.

Western Blotting

Various cell lines were extracted with Laemelli sample buffer and fractionated by SDS-PAGE. The proteins were then transferred onto PVDF membrane which was probed with the anti-PI3K-C2α antisera. After washing, the blots were incubated with goat-anti-rabbit HRP antibody and proteins were visualised by ECL (Amersham).

Subcellular Fractionation of PI3K-C2α

The subcellular distribution of endogenous PI3K-C2α protein was examined by differential centrifugation of cell homogenates. Cells were disrupted either by dounce homogenisation or 10 passages through a 25 gauge needle in Tris/sucrose buffer (0.25M sucrose, 20 mM Tris/HCl pH 7.4, 1 mM sodium orthovanadate, 1 mM PMSF, 10 µg/ml leupeptin, 200 KIU/ml aprotonin, 1 µg/ml antipain, 400 µg/ml benzamidine and 1 µg/ml pepstatin). The homogenate (homog) was centrifuged at 3000 g for 10 minutes to remove nuclei and unbroken cells. The supernatant(s/n) was spun at 18000 g to obtain the plasma membrane fraction pm) and the resultant supernatant centrifuged for an additional 30 minutes at 350000 g. The pellet obtained was termed the low density microsomal fraction (LDM) and the supernatant cytosol (cyt). All manipulations were performed at 4° C. Fractions were extracted in Laemelli sample buffer, analysed by SDS-PAGE and visualised by western blotting.

Monkey Kidney Cos cells were transiently transfected with a 5' and 3' glu tagged PI3K-C2α construct ligated in a pMT-SM vector. These cells were used 48 hours following electroporation. For fractionation studies, proteins were visualised by a anti-glu tag monoclonal antibody following western blotting. These cells were also used to examine the localisation of the PI3K-C2α protein by confocal microscopy. For this purpose, electroporated cells were plated onto glass cover slips. After 48 hours, the cells were fixed, permeabilised and incubated with anti-glu tag monoclonal antibody for two hours. Cells were then washed and incubated with anti-mouse FITC coupled antibody. The staining pattern was then examined using a Zeiss confocal microscope.

Assay of PI 3-kinase Activity

Typically, PI 3-kinase assays were performed in a total volume of 50 µl containing 20 mM Hepes pH7.4. 100 mM NaCl, 0.1 mM EGTA, 0.1%—mercaptoethanol, and 200 µM phosphoinositide. After preincubating sonicated lipid with sample for 10 minutes, the reactions were initiated upon the addition of 2.5 mM MgCl$_2$, 100 mM ATP (0.2µCiγ$[^{32}P]$ ATP). Assays were incubated at 30° C. for 20 minutes and terminated with acidified chloroforn:methanol. The extracted lipid products were analysed by thin layer chromatography using Silica gel 60 plates and chloroform:methanol:4M ammonium hydroxide (45:35:10) for assays examining phosphorylation of PtdIns. When separation of PtdIns 3P, PtdIns (3,4)P$_2$ and PItdIns (3,4,5)P$_3$ was required, propan-1-ol: 2M acetic acid (65:35) was used. Phosphorylated lipids were visualised by either autoradiography or by phosphoimage analysis (Molecular Dynamics). Assays were linear with respect to time and enzyme addition.

Characterisation of PI 3K-C2α Reaction Products by HPLC

Phosphorylation of PI was performed using recombinant protein as described above. The reaction products were extracted in acidified chloroform: methanol and deacylated with methylamine (46). HPLC analysis of glycerophosphoinositols was performed using a PARTISPHERE SAX column (Whatman International) and eluted using a linear gradient of 1M (NH$_4$)$_2$ HPO $_4$ (pH3.8) against water at 1 ml min$^{-1}$. Radioactive peaks were detected using an in-line detector (Reeve Analytical).

Results

Cloning of PI3K-C2α

Degenerate primers and mRNA from the human cell line U937 were used to produce a number of partial cDNAs by RT-PCR. One product of these reactions was found to be a novel cDNA which was then used to screen a λ Zap cDNA library made from U937 cells. Twenty seven positive clones selected from 3×10⁶ plaques were obtained following tertiary screening. A 6.1 kb clone was sequenced and found to contain an open reading frame of 4618 nucleotides which could encode a putative catalytic domain. Since no definitive 5' Kozak consensus sequence was found in this clone (24), RACE PCR was performed using cDNA from U937 cells. A 643 nucleotide extension to the original cDNA was generated. This cDNA fragment contained an ATG sequence which was in frame with the longest open reading frame of the parent clone and had an upstream stop codon. The RACE product was then ligated onto the parent clone to produce a composite cDNA of 5.1 kb which could encode a protein of 1686 amino acid residues that would have a calculated molecular mass of 190 kDa (FIG. 1).

Figure 2B:
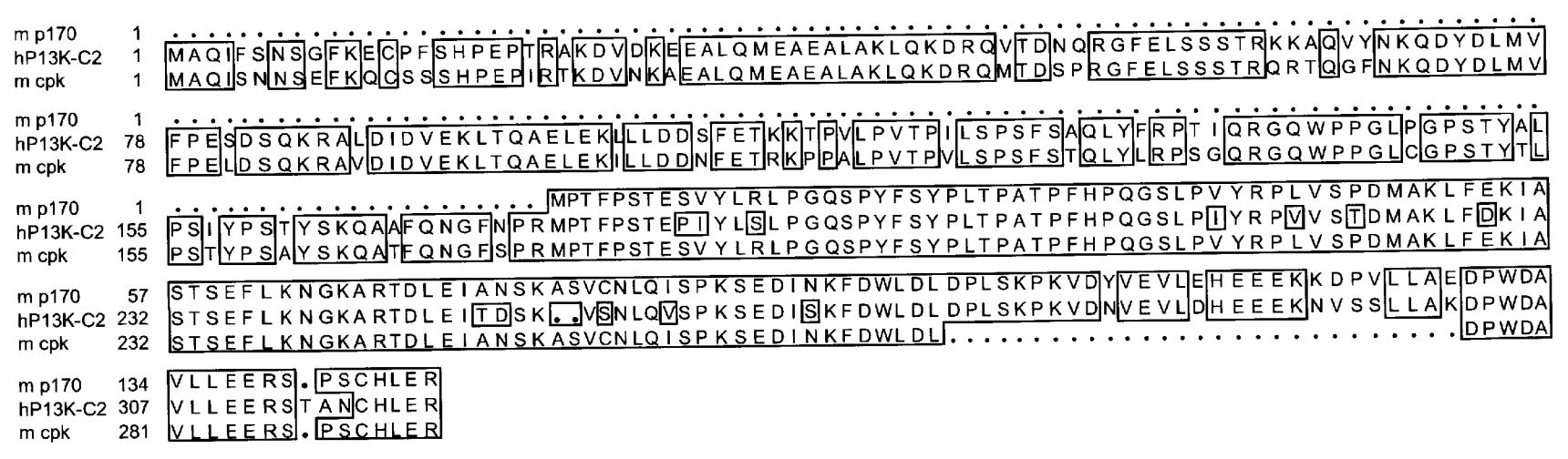
Figure 2C:
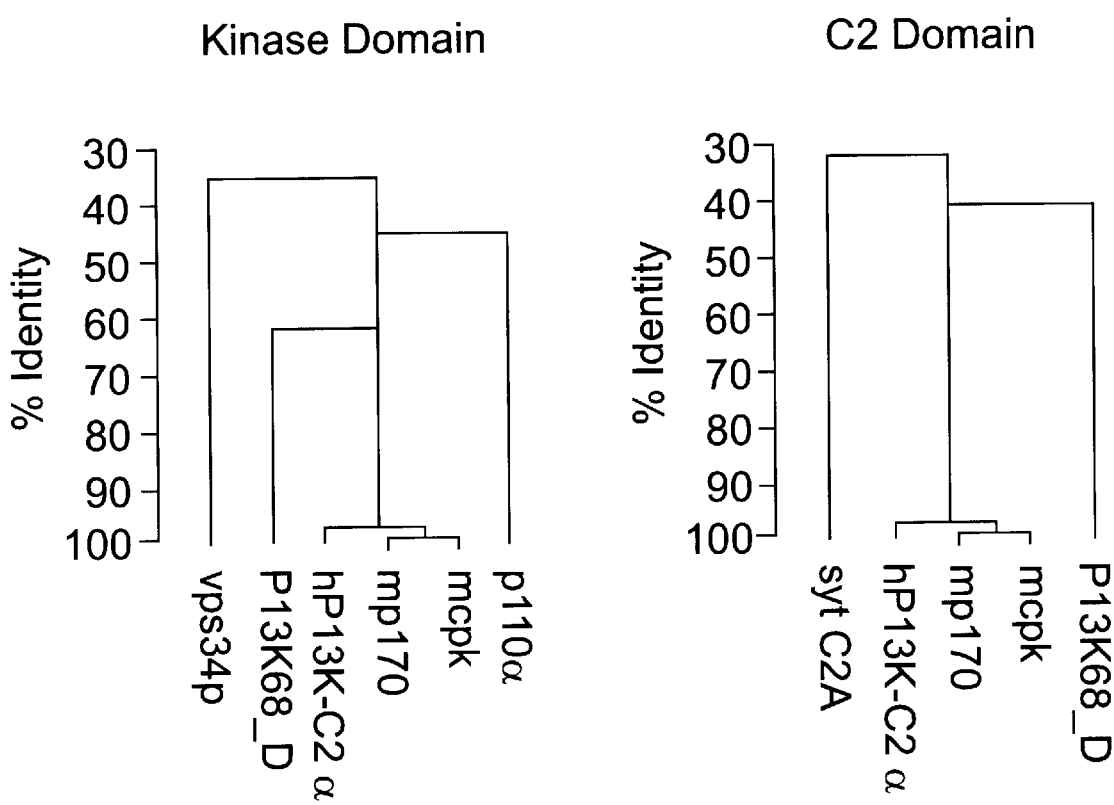

The protein which was termed PI3K-C2α, has an amino acid sequence which when optimally aligned, displays an overall sequence identity of 32.5% with the sequences of drosophila PI3K__68D and cpk (22,23) and 90.8% and 90.2% with those of the murine proteins mp170 (16) and mcpk (22) respectively (FIG. 2 upper panel). Two regions of amino acid sequence, HRI and HRII, define areas which have the greatest similarity to the sequences of other PI 3-kinases. The putative catalytic domain (HR1) is defined by residues 1137–1398 of the PI3K-C2α or α protein. Within this region, the amino acid sequence of PI3K-C2α is 62% identical to that of PI3K__68D and cpk, 97% to mp170 and 99.6% to mcpk (FIG. 2 lower panel). When the HR1 domain of PI3K-C2α is compared to that of p110α and PtdIns 3-kinase, sequence identity falls to only 45% and 35% respectively amino acid residues 871–1020 of PI3K-C2α define a region termed the PIK domain (HR2) which is also present in other lipid kinases as well as TOR2 (25). The function of this domain is currently unknown.

The amino acid sequence of the carboxy terminal region of PI3K-C2α (residues 1549–1686) shows strong sequence homology to a domain originally identified as a $Ca^{2+}$ and pjhospholipid-binding module in protein kinase C, which is termed the C2 domain (13). In this region, the PI3K-C2 amino acid sequence is 96% identical to that of the C2 domains identified in cpk-m and p170, 39% identical to the C2 domain of PI3K__68D and cpk and 32% and 24% identical to the C2A and C2B domains of synaptotagmin respectively (FIG. 2 lower panel). Within the amino terminal region, large insertions are necessary in the PI3K-C2α amino acid sequence to allow optimal alignment with that of Drosophila PI3K__68D and cpk. It is perhaps significant that the type II polyproline motif PPLPPR (SEQ ID NO:11) identified in PI3K__68D and cpk (residues 456–462) is absent in PI3K-C2α. Within this region however, numerous proline residues are evident. The amino terminus of PI3K-C2α lacks any clearly delineated regulatory domain.

Interestingly, alignment of the two murine amino acid sequences with that of PI3K-C2α shows that the p170 protein lacks the first 176 amino residues of the longer murine mcpk sequence. The mcpk protein has a 28 amino acid residues deletion in this region (residues 275–301 of the PI3K-C2α sequence) which is absent in both mp170 and PI3K-C2α (FIG. 2, middle panel). The significance of these sequence differences requires further investigation.

Tissue/Cell Expression of PI3K-C2α

Figure 3:
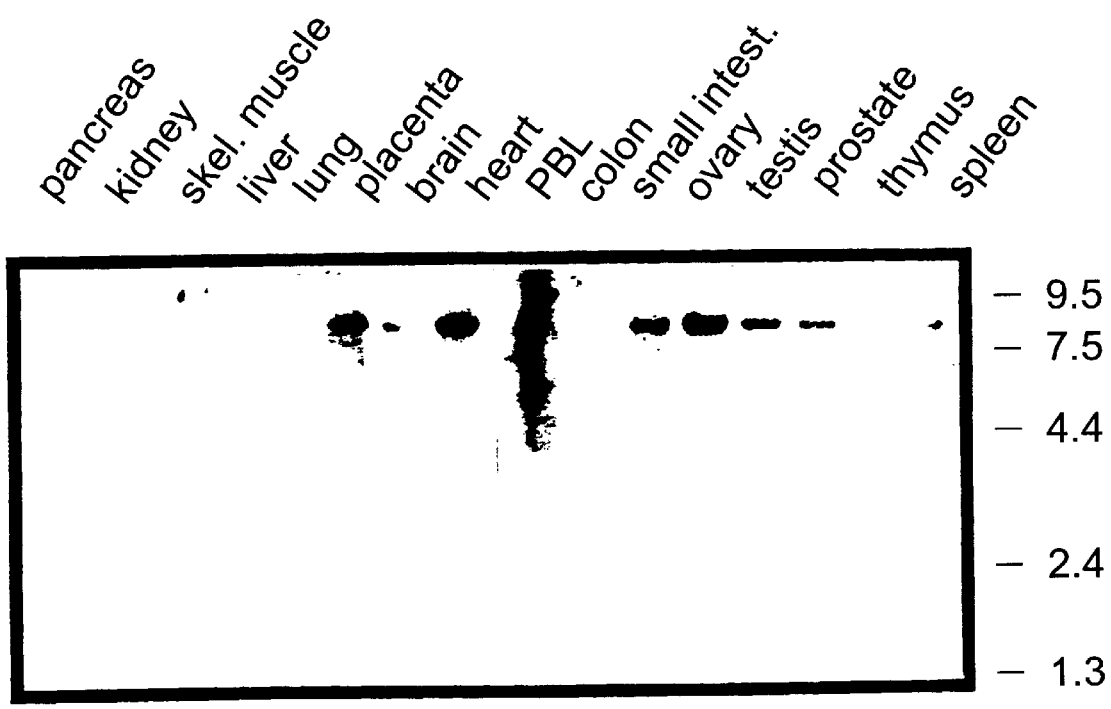
FIG. 3 represents a northern blot of the distribution of mRNA encoding PI3K-C2α in various tissues.

Northern blot analysis carried out using poly A+RNA isolated from human tissue revealed that the cDNA encoding human PI3K-C2α hybridised to a 8 kb species in the RNA from a wide variety of tissues (FIG. 3). Highest levels of expression were found in the heart, placenta and ovary. The mRNA was only undetectable in the kidney. The size of the mRNA is consistent with the length of the full length cDNA. In testes, an additional smaller transcript of approximately 6.5 kb was also present and could have arisen from differential splicing.

Figure 7:
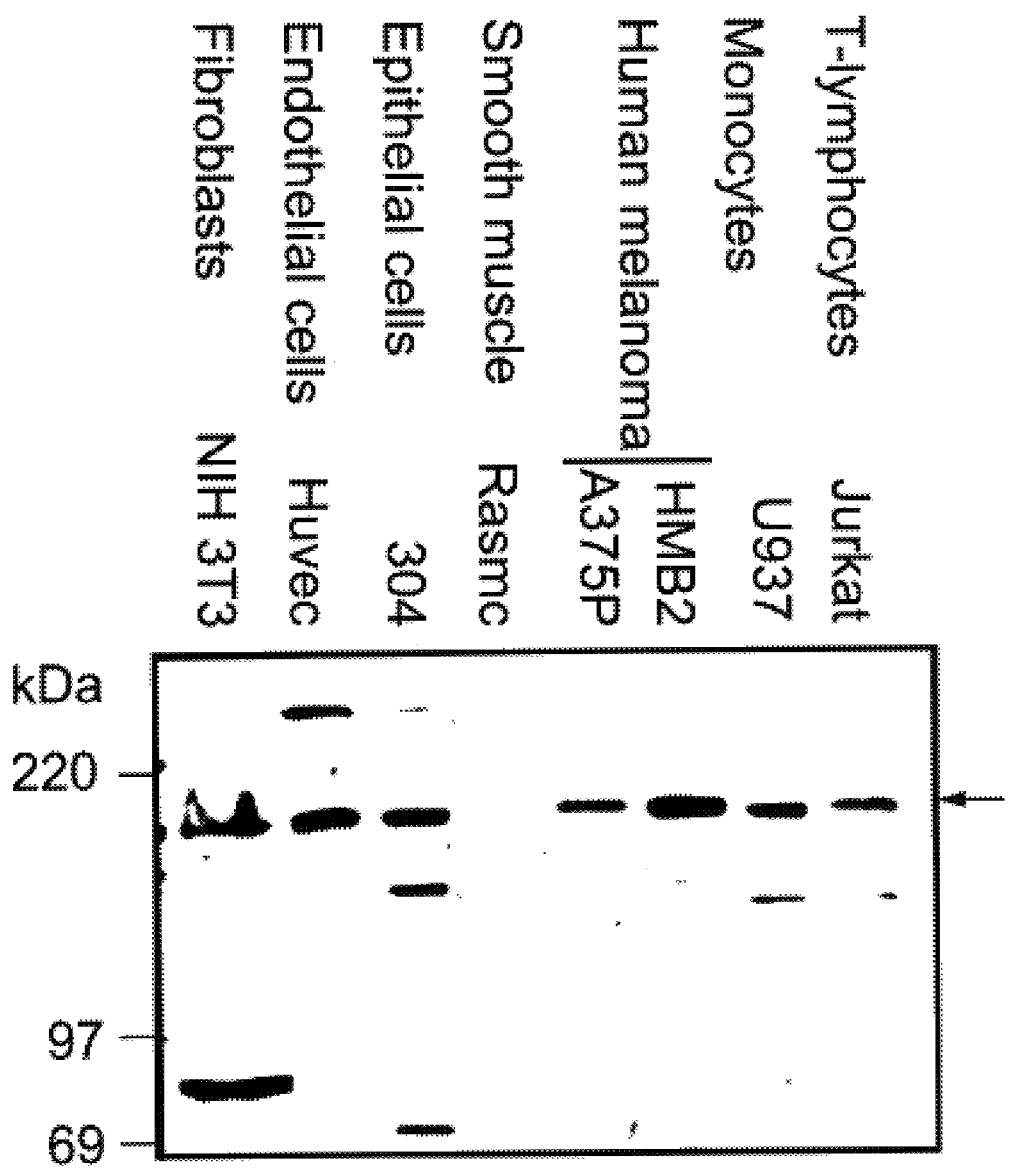
FIG. 7 represents a western blot of cell lysates prepared from various cell-lines and probed with antisera to PI3K-C2α.

Western blots of cell lysates from a variety of cell-lines using the anti-PI3K-C2α antisera confirms the presence of the 190 kDa polypeptide encoding PI3K-C2 in all cell-lines tested with the exception of the smooth muscle cell-line Rasmc, FIG. 7.

Characterisation of Lipid Substrate Specificity

Figure 4A:
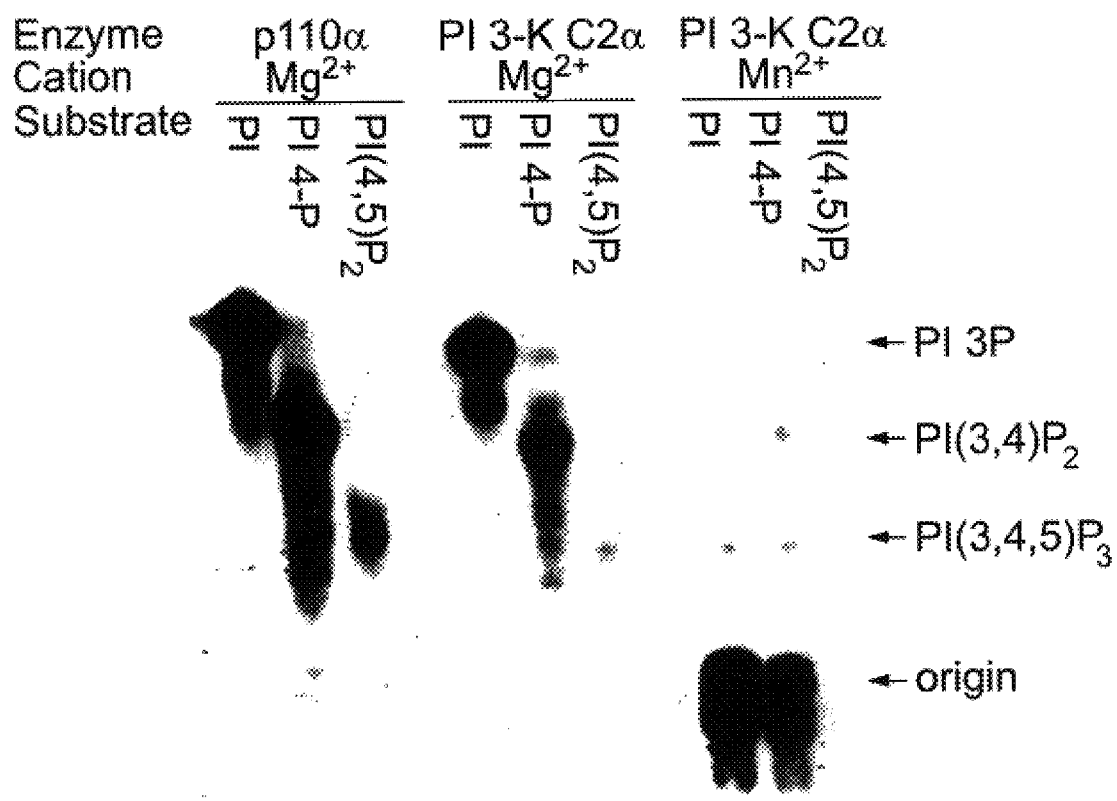
FIG. 4 represents the in vitro substrate specificity of PI3K-C2α in the presence of $Mg^{2+}$ and $Mn^{2+}$, p110α is included as a positive control.
Figure 4B:
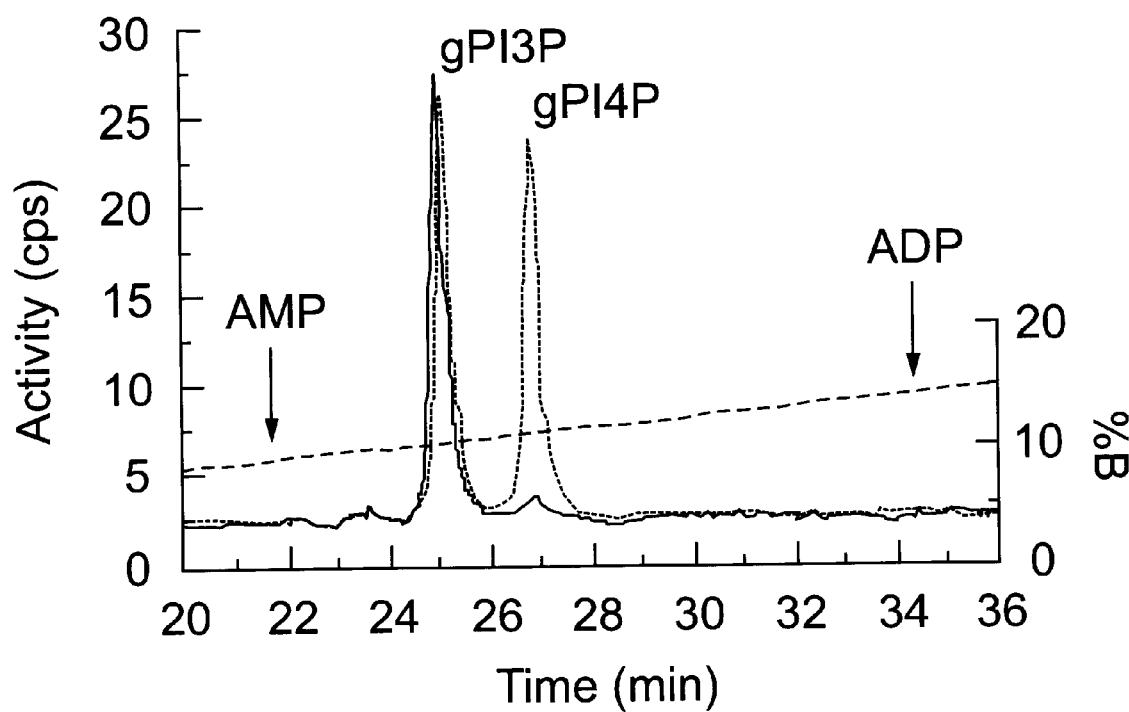

To allow biochemical analysis of PI3K-C2α, a recombinant baculovirus was produced. The construct generated encoded a fusion protein which comprised the amino acid sequence of GST linked to residues 148–1686 of the PI3K-C2α protein. Sf9 cells were infected with the virus and after 2 days, the expressed protein was purified using glutathione-sepharose beads. The enzymatic activity and substrate specificity were investigated and compared to that of GST-p110α expressed in the same system. In the presence of $Mg^{2+}$ p110α was able to utilise PtdIns, PtdIns(4)P and PtdIns(4,5)$P_2$ as substrates to produce PtdIns3P, PtdIns(3,4)$P_2$ and PtdIns(3,4,5)$P_3$ respectively (FIG. 4 upper panel). In contrast, PI3K-C2α was able to phosphorylate PtdIns and PtdIns(4)P but could not use PtdIns(4,5)$P_2$. Like p110, the lipid kinase activity of PI3K-C2α displayed a cation dependence for $Mg^{2+}$ and was found to be inactive in the presence of $Mn^{2+}$. This ion dependence of the enzyme activity of PI3K-C2α contrasts with that of the human Ptd Ins 3-kinase which shows a preference for $Mn^{2+}$ (14).

To confirm that PI3K-C2α could phosphorylate PtdIns at the D-3 position on the inositol ring, anion exchange HPLC was performed upon the deacylated reaction products. A single peak of radioactive glycerolphosphate was obtained which co-eluted with the deacylated PtdIns 3-P produced by the action of recombinant p110α upon Ptd Ins (FIG. 4 lower panel). No additional products were observed confirming that PI3K-C2 specifically phosphorylates phosphatidylinositides at the D-3 position of their inositol ring.

Sensitivity to Inhibitors of PI 3-kinase Activity

Figure 5:
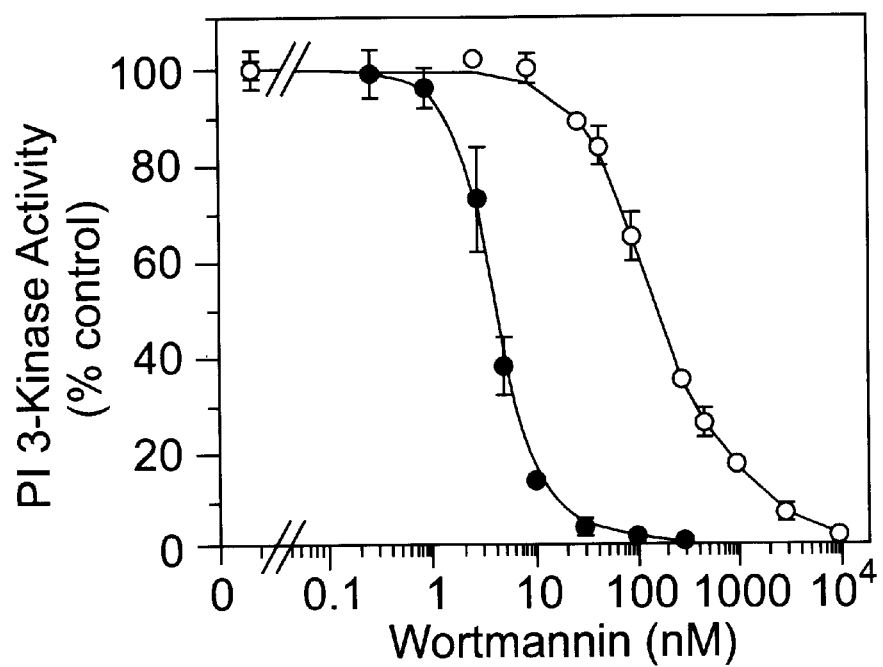
FIG. 5 represents the resistance of recombinant PI3K-C2α to the PI3-kinase inhibitors Wortmannin (Panel A) and LY 294002 (Panel B) (p110α=●, recombinant PI3K-C2α=○)
Figure 5:
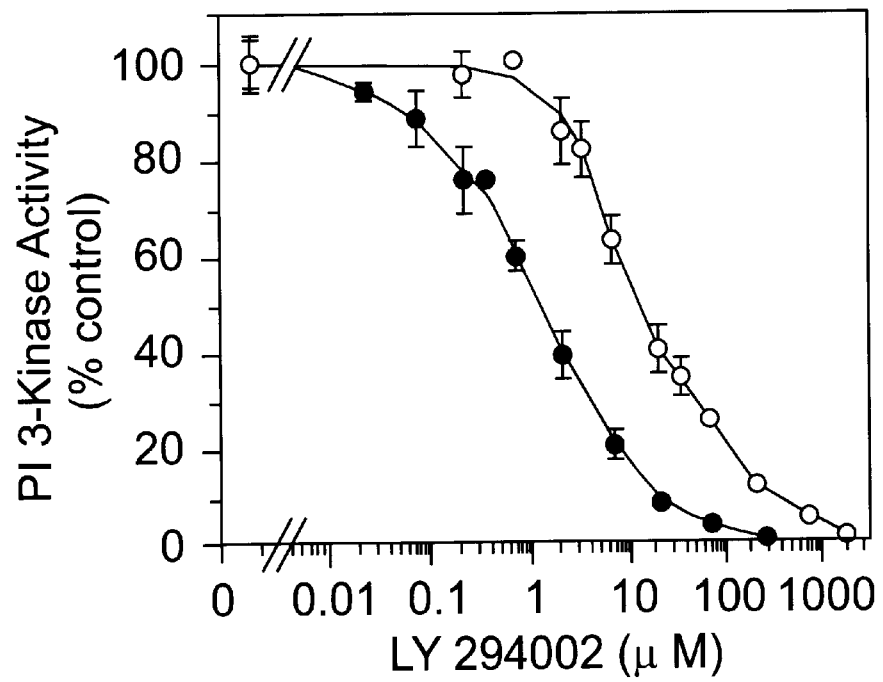

The compounds Wortmannin and LY294002 (2-(4-morpholinyl)-8-phenyl-4H-1-benzopyran-4-one) have been used extensively to assess the involvement of PI 3-kinase in many different physiological processes. To date, all cloned human PI 3-kinases have been found to be sensitive to Wortmannin action at nanomolar concentrations. The effect of these inhibitors on the lipid kinase activity of PI3K-C2α was examined, using PtdIns as a substrate, in the presence of increasing concentrations of each inhibitor. In agreement with previous studies, p110α activity was found to be sensitive to Wortmannin at low nM concentrations ($IC_{50}$=3 nM) with maximal attenuation of activity obtained at 100 nM (FIG. 5A). In contrast, the observed $IC_{50}$ using PI3K-C2α was 200 nM with maximal inhibition only obtained using Wortmannin at 10 μM. For LY294002, the $IC_{50}$ using p110α was 1.5 mM and maximal inhibition was obtained at 300 μM (FIG. 5B). Again PI3K-C2α was less sensitive than p110α to the action of the inhibitor ($IC_{50}$=20 μM). The lipid kinase activity of PI3K-C2α was maximally attenuated using 2 mM LY294002.

Subcellular Localisation of PI3K-C2α in Monkey Kidney Cos Cells

Figure 6:
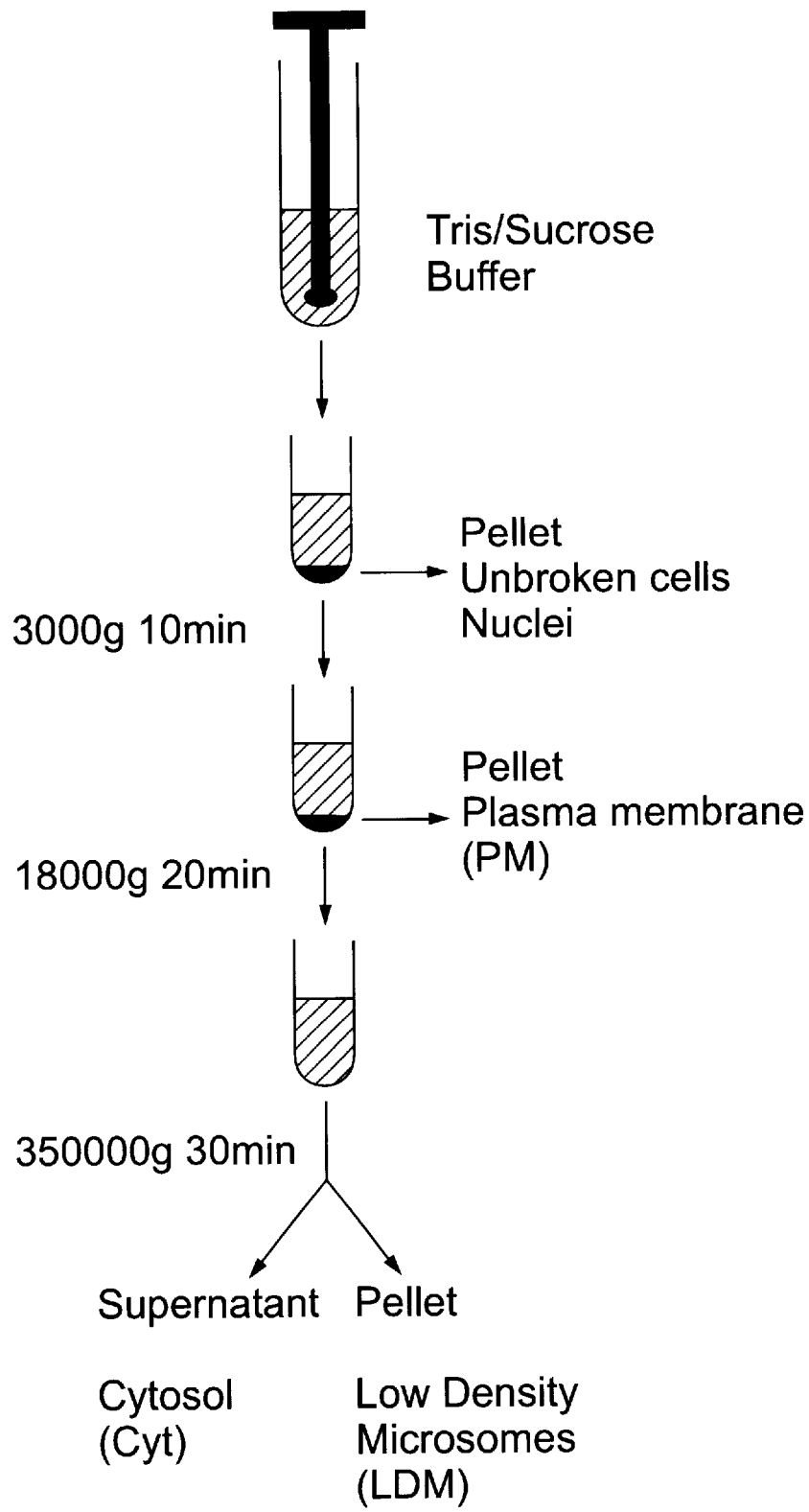
FIG. 6 is a diagrammatic representation of the sub-cellular fractionation of Cos 7 cells into various membrane fractions.
Figure 8:
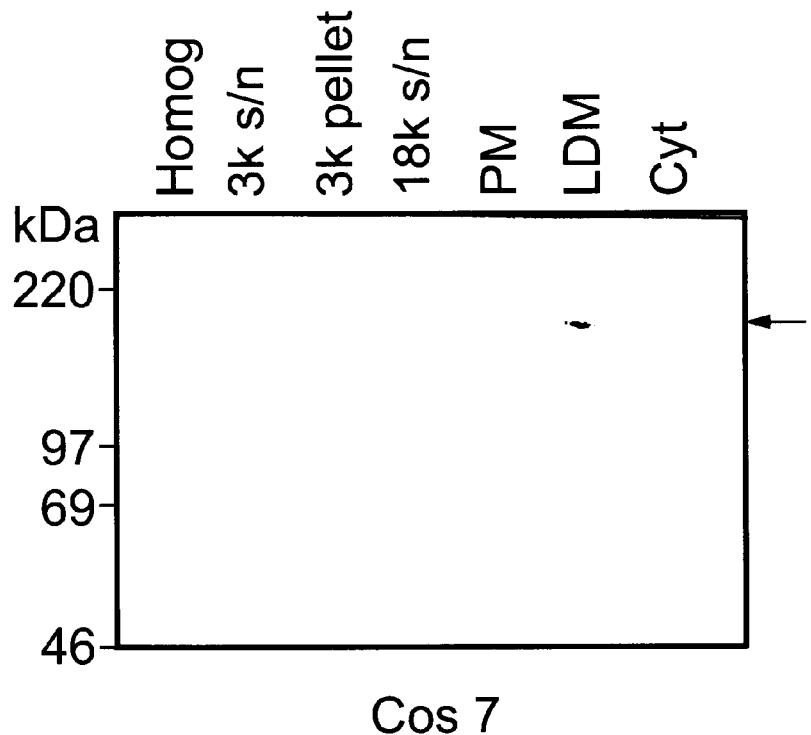
FIG. 8 represents a western blot of sub-cellular fractions prepared from Cos 7 cells and probed with antisera to PI3K-C2α.
Figure 8:
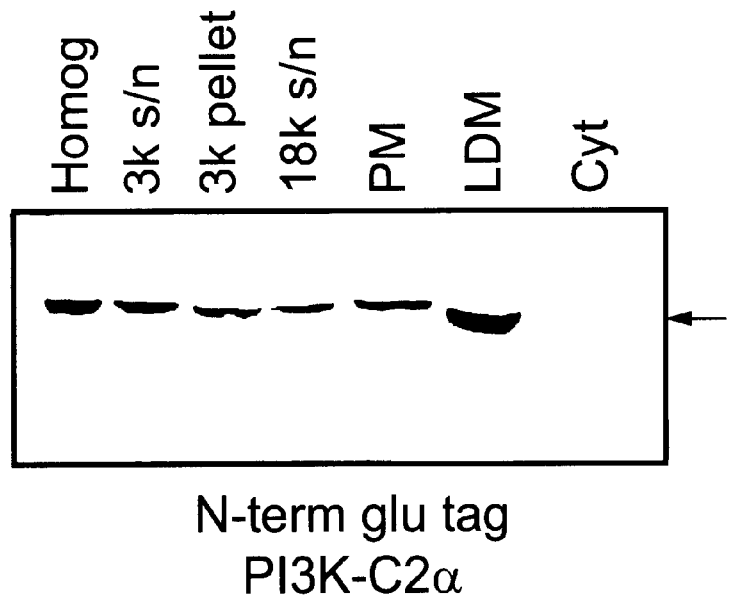
Figure 9:
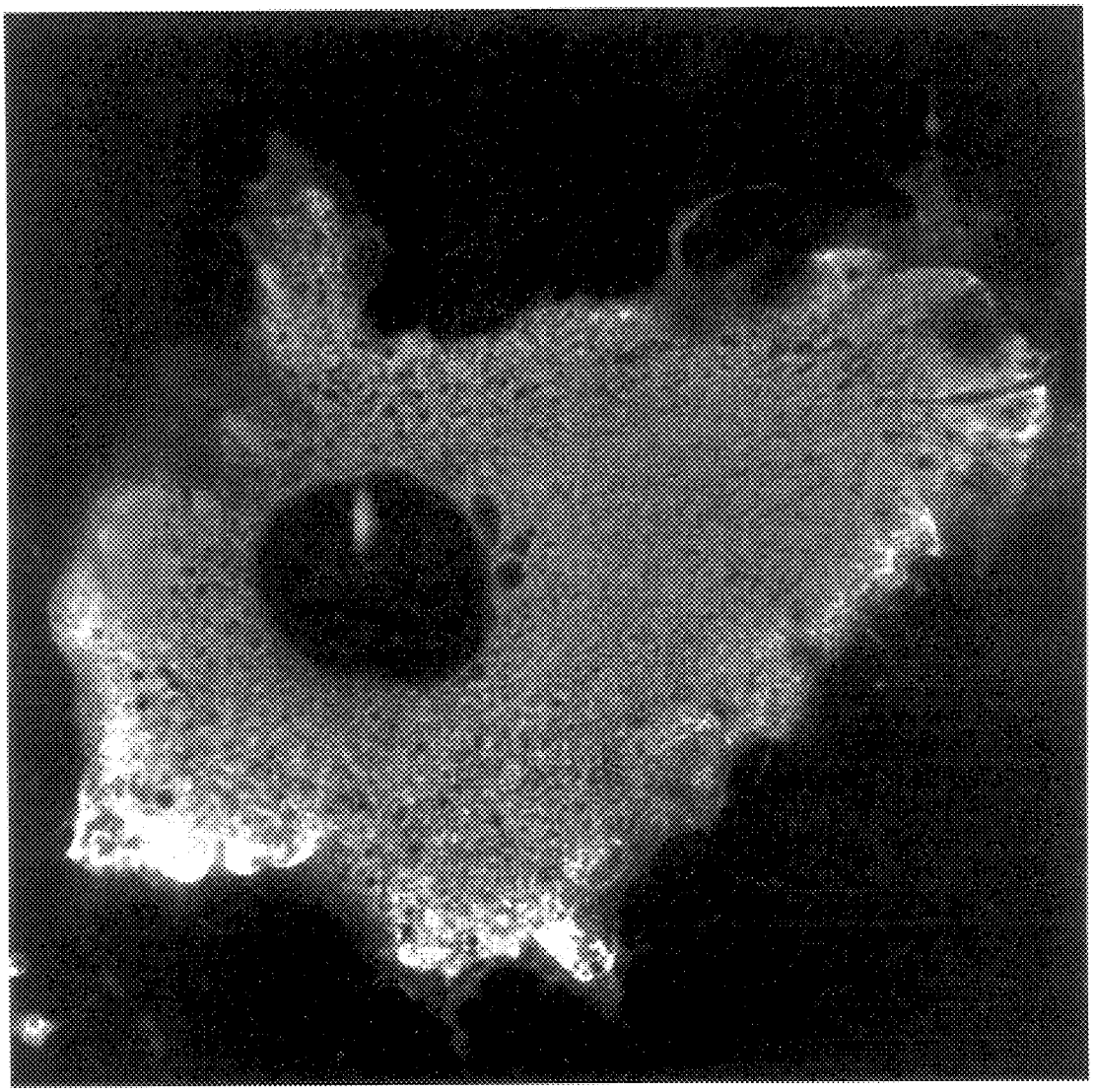
FIG. 9 represents an immunofluoresence image of Cos7 cells expressing recombinant glu-tagged PI3K-C2α.

To determine the subcellular location of PI3K-C2α, Monkey Kidney Cos cells were subjected to physical disruption followed by fractionation by differential centrifugation, FIG. 6. FIG. 7 shows a western blot of various subcellular fractions prepared as described in materials and methods. A significant enrichment of PI3K-C2α polypeptide is shown in the LDM fraction when using the anti-amino terminus antisera, see FIG. 8 A. This enrichment is also reflected, although to a lesser extent, when using cell fractions prepared from electroporated Monkey Kidney Cos cells expressing glu tagged PI3K-C2α, see FIG. 8 B. The nature of the affinity of PI3K-C2α for microsomal membranes is currently unkown.

Discussion

In the present study the cloning and biochemical characterization of PI3K-C2α, a novel human PI 3-kinase of 190 kDa is described. Based on the presence of a C-terminal C2 domain and the phospholipid substrate specificity of PI3K-C2α, this enzyme like Drosophila PI3K_68D (23), cpk (22) and the two murine PI 3-kinases mp170 (16) and mcpk (22) can be defined as a class II PI 3-kinase (26) (FIG. 2).

The amino acid sequence of PI3K-C2α is 90.8% and 90.2% identical to that of two recently cloned murine PI 3-kinases mp170 (16) and mcpk respectively (22). This level of sequence identity suggests that PI3K-C2α is the human homologue of a single mouse PI3-kinase termed mp170 (27) or mcpk (28) which is encoded by the same gene. Despite the overall sequence identity between human PI3K-C2α and murine mp170 and mcpk, alignment of their N-termini shows that mp170 lacks the first 175 amino acid residues of both PI3K-C2α and cpk-m (FIG. 2). In this region mcpk lacks 28 amino acid residues which are present in both PI3K-C2α and mp170. Analysis of the two murine cDNAs suggests that these differences in the proteins may be the result of differential splicing of a single gene.

The putative catalytic domain (HRI) and the PIK domain (HR II) of PI3K-C2α are related to similar regions found in all Class I, II and III PI3-kinases. However, PI3K-C2α appears to lack any clear consensus sequences which would delineate other functional domains. For example, PI3K-C2α lacks the amino terminal motif present in p110α, p110β and p110δ which mediates binding to p85 adaptors (29). Furthermore, PI3K-C2α does not contain the type II polyproline motif previously identified in PI3K_68D and cpk, although it does contain a large number of proline residues which might allow an interaction with SH3 domain-containing proteins through a non consensus binding motif (30).

The class II PI3-kinases are in part characterised by their C-terminal C2 domain. C2 domains were originally identified in protein kinase C where they were shown to mediate $Ca^{2+}$-dependent phospholipid binding (13). Subsequently, C2 domains, often occurring in tandem, have also been defined in a variety of other proteins including synaptotagmin, rabpbillin 2A and cytosolic phospholipase A2 (31). In these proteins the C2 domain may confer similar biochemical properties. Functional heterogeneity has however, been observed amongst isolated C2 domains despite their high degree of sequence similarity. In addition to phospholipid binding, Ca2+ stimulates an association between synaptotagmin and syntaxin through the first C2A domain (32). In contrast, the second C2B domain is inactive in these assays suggesting that its function is not regulated by intracellular $Ca^{2+}$ levels. Indeed, the second C2 domain of synaptotagmin was shown to display a $Ca^{2+}$ independent binding to clathrin AP2 and polyinositol phosphates (33, 34). Recent studies have since demonstrated however, that the second C2 domain of synaptotagmin can also respond in a $Ca^{2+}$ triggered manner mediating a dimerization event (35, 36). Studies using a GST-fusion protein of the PI3K_68D C2 domain demonstrated that, like the second C2 domain of synaptotagmin, it was only able to bind acidic phospholipids in a cation independent manner (23). It will be of interest to determine if the biochemical properties of the PI3K-C2α domain are more similar to the first or the second synaptotagmin C2 domain.

The biochemical analysis described here has shown that in vitro PI3K-C2α can phosphorylate both Ptd Ins and Ptd Ins (4)P in the D3 position of the inositol ring (FIG. 4). These findings are consistent with the enzyme having a lipid specificity similar to that of PI3K_68D and cpk (23), (22). The substrate specificity of the mouse homologue has only been reported by Virbasius et al who concluded that Ptd Ins was the major lipid substrate of mp170 in vitro since they found that PtdIns(4)P was only very poorly phosphorylated by their enzyme (16). These results are somewhat surprising considering the degree of sequence identity between the catalytic domains of PI3K-C2α and mp170 (FIG. 2). One explanation for this difference could be that Virbasius et al used a crude brain lipid extract substrate in contrast to the purified lipid preparations we have used in the analysis of substrate specificity (16). Although it could be argued that use of the crude extract may be more physiological, it does not allow for an accurate quantitative comparison of the lipids present in the two preparations. Under these circumstances, a comparative assessment of the efficiency with which an enzyme could utilize a particular lipid substrate cannot be made accurately. Furthermore, a crude lipid preparation may contain factors which influence the lipid kinase activity of the recombinant protein.

The involvement of PI3-kinases in various processes of cell physiology has relied more and more on the use of the inhibitors Wortmannin and LY294002. Although initially described as an inhibitor of myosin light chain kinase at micromolar concentrations (37), Wortmannin was later shown to potently inhibit PDGF receptor-associated PI 3-kinase activity at 100 fold lower concentrations (2–5 nanomolar). Used in the low nanomolar range, Wortmannin was shown to block the generation of 3-phosphorylated lipids both in vitro and in whole cells such as murine fibroblasts (38). On the basis of such findings, Wortmannin began to be used extensively as a specific inhibitor of PI 3-kinase activity thereby implicating the formation of 3-phosphorylated lipids in a number of physiological responses. When the effect of Wortmannin on the lipid kinase activity of recombinant PI3K-C2α was examined we found that the concentrations of Wortmannin required to inhibit PI3K-C2α activity were more similar to those previously used to inhibit myosin light chain kinase ($IC_{50}$= 170–200 nM) (37, 39). Similarly, data presented using the mp170 enzyme suggests that it is also less sensitive to Wortmannin treatment than p110α (16). LY294002 is a structurally unrelated inhibitor of PI 3-kinase activity and PI3K-C2α is also less sensitive than p110α to this inhibitor. The difference in sensitivity between PI3K-C2α and p110α is however, only approximately one order of magnitude. The relevance of this differential sensitivity is unclear. Studies using p110α have shown that Wortmannin inactivates kinase activity by a covalent modification of Lys-802, a residue involved in the phosphate transfer reaction (40). This residue is present in all PI 3-kinase family members including PI3K-C2α. Further molecular modelling and structural studies may elucidate the nature of this Wortmannin resistance. These results with PI3K-C2α contrast not only with those derived from studies of Class I and III human PI 3-kinases but also to those obtained with the Drosophila PI3K_68D which displays a sensitivity to Wortnannin which is similar to that of p110α (23). The concentrations of both Wortmannin and LY294002 required to abolish PI3K-C2α activity are therefore likely to have precluded its inhibition in many experiments where PI 3-kinase activity has been studied. These findings may thus require many investigators to re-evaluate a possible involvement of PI3-kinase action in their physiological studies. Questions relating to the precise role PI3K-C2α plays in cells will consequently be hampered by the absence of suitable inhibitors of its lipid kinase activity.

REFERENCES

1. Schu, P. V., Takegawa, K., Fry, M. J., Stack, J. H., Waterfield, M. D., and Emr, S. D. (1993) Science 260, 88–92.
2. Davidson, H. W. (1995) J Cell Biol 130, 797–805.
3. Wennstrom, S., Hawkins, P., Cooke, F., Hara, K., Yonezawa, K., Kasuga, M., Jackson, T., Claesson Welsh, L., and Stephens, L. (1994) Curr Biol 4, 385–93.
4. Valius, M., and Kazlauskas, A. (1993) Cell 73, 321–34.
5. Cantley, L. C., Auger, K. R., Carpenter, C., Duckworth, B., Graziani, A., Kapeller, R., and Soltoff, S. (1991) Cell 64, 281–302.
6. Aagaard Tillery, K. M., and Jelinek, D. F. (1996) J Immunol 156, 4543–54.
7. Jackson, T. R., Stephens, L. R., and Hawkins, P. T. (1992) J Biol Chem 267, 16627–36.
8. Auger, K. R., Serunian, L. A., Soltoff, S. P., Libby, P., and Cantley, L. C. (1989) Cell 57, 167–175.
9. Morgan, S. J., Smith, A. D., and Parker, P. J. (1990) Eur. J. Biochem. 191, 761–767.
10. Hu, P., Mondino, A., Skolnik, E. Y., and Schlessinger, J. (1993) Mol Cell Biol 13, 7677–88.
11. Vanhaessebrock et al. (manuscript submitted, not yet published).
12. Stephens, L., Hawkins, P. T., Eguinoa, A., and Cooke, F. (1996) Phil. Trans. R. Soc. Lond. 351, 211–5.
13. Kaibuchi, K., Fukumoto, Y., Oku, N., Takai, Y., Arai, K., and Muramatsu, M. (1989) J Biol Chem 264, 13489–96.
14. Volinia, S., Dhand, R., Vanhaesebroeck, B., MacDougall, L. K., Stein, R., Zvelebil, M. J., Domin, J., Panaretou, C., and Waterfield, M. D. (1995) EMBO J 14, 3339–48.
15. Panaretou et al. (manuscript submitted, not yet published).
16. Virbasius, J. V., Guilherme, A., and Czech, M. P. (1996) J Biol Chem 271, 13304–13307.
17. Ui, M. (1984) Trends Pharmacol. Sci. 5, 277–279.
18. Bagglollnl, M. et al. (1987) Exp. Cell Res. 169, 408–418.
19. Dewald, B., Thelen, M. and Bagglollnl, M. (1988) J Biol Chem. 263, 16179–16184.
20. Ui, M. Okada, T., Hazeki, K. and Hazeki, O. (1995) TIBS 20, 303–307.
21. Kanal, F. et al, (1993) Biochem. Biophys. Res. Commun. 195, 762–768.
22. Molz, L., Chen, Y. W., Hirano, M., and Williams, L. T. (1996) J Biol Chem 271, 13892–99.
23. MacDougall, L. K., Domin, J., and Waterfield, M. D. (1995) Curr. Biol. 5, 1404–1415.
24. Kozak, M. (1991) J Biol Chem 266, 19867–70.
25. Flanagan, C. A., Schnieders, E. A., Emerick, A. W., Kunisawa, R., Admon, A., and Thorner, J. (1993) Science 262, 1444–8.
26. Domin, J. and Waterfield, M.D. (1997) FEBS Letts 410, 91–95.
27. Stephens, L., Smrcka, A., Cooke, F. T., Jackson, T. R., Sternweis, P. C., and Hawkins, P. T. (1994) Cell 77, 83–93.
28. Stoyanov, B., Volinia, S., Hanck, T., Rubio, I., Loubtchenkov, M., Malck, D., Stoyanova, S., Vanhaesebroeck, B., Dhand, R., Nurnberg, B., Gierschik, P., Seedorf, K., Hsuan, J. J., Waterfield, M. D., and Wetzker, R. (1995) Science 269, 690–693.
29. Dhand, R., Hara, K., Hiles, I., Bax, B., Gout, I., Panayotou, G., Fry, M. J., Yonezawa, K., Kasuga, M., and Waterfield, M. D. (1994) EMBO J. 13, 511–521.
30. Gout, I., Dhand, R., Hiles, I. D., Fry, M. J., Panayotou, G., Das, P., Truong, O., Totty, N. F., Hsuan, J., Booker, G. W., Campbell, I. D., and Waterfield, M. D. (1993) Cell 75, 25–36.
31. Ponting, C. P., and Parker, P. J. (1996) Protein Sci 5, 162–166.
32. Li, C., Davletov, B. A., and Sudhof, T. C. (1995) J Biol Chem 270, 24898–902.
33. Zhang, J. Z., Davletov, B. A., Sudhof, T. C., and Anderson, R. G. (1994) Cell 78, 751–60.
34. Fukuda, M., Kojima, T., Aruga, J., Niinobe, M., and Mikoshiba, K. (1995) J Biol Chem 270, 26523–7.
35. Chapman, E. R., An, S., Edwardson, M., and Jahn, R. (1996) J Biol Chem 271, 5844–5849.
36. Sugita, S., Hata, Y., and Sudhof, T. C. (1996) J Biol Chem 271, 1262–5.
37. Nakanishi, S., Kakita, S., Takahashi, I., Kawahara, K., Tsukuda, E., Sano, T., Yamada, K., Yoshida, M., Kase, H., Matsuda, Y., and et al. (1992) J Biol Chem 267, 2157–63.
38. Powis, G., Bonjouklian, R., Berggren, M. M., Gallegos, A., Abraham, R., Ashendel, C., Zalkow, L., Matter, W. F., Dodge, J., Grindey, G., and et al. (1994) Cancer Res 54, 2419–23.
39. Yano, H., Nakanishi, S., Kimura, K., Hanai, N., Saitoh, Y., Fukuii, Y., Nonomura, Y., and Matsuda, Y. (1993) J Biol Chem 268, 25846–56.
40. Wymann, W. P., Bulgarelli-Leva, G., Zvelebil, M. J., Pirola, L., Vanhaesebroeck, B., Waterfield, M. D., and Panayotou, G. (1996) Mol Cell Biol 16, 1722–33.

What is claimed is:

1. An isolated nucleic acid comprising:
   (a) a nucleotide sequence that encodes human PI3K-C2α having the amino acid sequence of SEQ ID NO:2.

2. The isolated nucleic acid of claim 1 wherein the nucleotide sequence is SEQ ID NO:1.

3. The isolated nucleic acid of claim 1 which is a cDNA.

4. An isolated nucleic acid that hybridizes to SEQ ID NO:1 in 0.5 M sodium phosphate, pH 7.2, 7% SDS, 1 mM EDTA at 65° C. and remains bound after two washing steps with 0.5×SSC and 0.1% SDS for 20 minutes at 60° C.; wherein the isolated nucleic acid encodes a protein kinase that
   (a) has an increased resistance to PI3K-kinase inhibitors Wortmannin and LY294000 relative to the P13K kinase, p110α;
   (b) lacks a p85 binding site; and
   (c) is missing the polyproline motif consisting of SEQ ID NO:11, which is characteristic of type II P13-kinases.

5. The isolated nucleic acid of claim 4 which is a cDNA.

6. A recombinant vector that expresses human P13K-C2α in a prokaryotic or a eukaryotic cell comprising:
   (a) a nucleotide sequence that encodes human P13K-C2α having the amino acid sequence of SEQ ID NO:2; and
   (b) a DNA promoter element; wherein the nucleotide sequence is functionally linked to said promoter element.

7. The recombinant vector of claim 6 wherein said DNA promoter element allows the inducible expression of human P13K-C2α in the prokaryotic or the eukaryotic cell.

8. The recombinant vector of claim 6 wherein said DNA promoter element allows the repressible expression of human P13K-C2α in the prokaryotic or the eukaryotic cell.

9. The recombinant vector of claim 6 wherein said DNA promoter element allows the constitutive expression of human P13K-C2α in the prokaryotic or the eukaryotic cell.

10. The recombinant vector of claim 6 wherein said DNA promoter element is a tissue specific and/or cell specific promoter element.

11. A recombinant vector that expresses human P13K-C2α in a prokaryotic or a eukaryotic cell comprising:
   (a) an isolated nucleic acid that hybridizes to SEQ ID NO:1 in 0.5 M sodium phosphate, pH 7.2, 7% SDS, 1 mM EDTA at 65° C. and remains bound after two washing steps with 0.5×SSC and 0.1% SDS for 20 minutes at 60° C.;
      wherein the isolated nucleic acid encodes a protein kinase that
         (i) has an increased resistance to PI3K-kinase inhibitors Wortmannin and LY294000 relative to the P13K kinase, p110α;
         (ii) lacks a p85 binding site; and
         (iii) is missing the polyproline motif consisting of SEQ ID NO:11, which is characteristic of type II P13K-kinases; and
   (b) a DNA promoter element; wherein the nucleotide sequence is functionally linked to said promoter element.

12. The recombinant vector of claim 11 wherein said DNA promoter element allows the inducible expression of human P13K-C2α in the prokaryotic or the eukaryotic cell.

13. The recombinant vector of claim 11 wherein said DNA promoter element allows the repressible of human P13K-C2α in the prokaryotic or the eukaryotic cell.

14. The recombinant vector of claim 11 wherein said DNA promoter element allows the constitutive expression of human P13K-C2α in the prokaryotic or the eukaryotic cell.

15. The recombinant vector of claim 11 wherein said DNA promoter element is a tissue specific and/or cell specific promoter element.

16. An isolated polypeptide encoding human P13K-C2α that comprises the amino acid sequence of SEQ ID NO:2.

* * * * *

SEQUENCE LISTING

```
<160> NUMBER OF SEQ ID NOS: 11

<210> SEQ ID NO 1
<211> LENGTH: 5061
<212> TYPE: DNA
<213> ORGANISM: Homo sapiens
<220> FEATURE:
<221> NAME/KEY: CDS
<222> LOCATION: (1)..(5058)
<223> OTHER INFORMATION:

<400> SEQUENCE: 1
```

-continued

```
atg gct cag ata ttt agc aac agc gga ttt aaa gaa tgt cca ttt tca      48
Met Ala Gln Ile Phe Ser Asn Ser Gly Phe Lys Glu Cys Pro Phe Ser
 1               5                  10                  15 cat ccg gaa cca aca aga gca aaa gat gtg gac aaa gaa gaa gca tta      96
His Pro Glu Pro Thr Arg Ala Lys Asp Val Asp Lys Glu Glu Ala Leu
             20                  25                  30 cag atg gaa gca gag gct tta gca aaa ctg caa aag gat aga caa gtg    144
Gln Met Glu Ala Glu Ala Leu Ala Lys Leu Gln Lys Asp Arg Gln Val
         35                  40                  45 act gac aat cag aga ggc ttt gag ttg tca agc agc acc aga aaa aaa    192
Thr Asp Asn Gln Arg Gly Phe Glu Leu Ser Ser Ser Thr Arg Lys Lys
 50                  55                  60 gca cag gtt tat aac aag cag gat tat gat ctc atg gtg ttt cct gaa    240
Ala Gln Val Tyr Asn Lys Gln Asp Tyr Asp Leu Met Val Phe Pro Glu
 65                  70                  75                  80 tca gat tcc caa aaa aga gca tta gat att gat gta gaa aag ctc acc    288
Ser Asp Ser Gln Lys Arg Ala Leu Asp Ile Asp Val Glu Lys Leu Thr
             85                  90                  95 caa gct gaa ctt gag aaa cta ttg ctg gat gac agt ttc gag act aaa    336
Gln Ala Glu Leu Glu Lys Leu Leu Leu Asp Asp Ser Phe Glu Thr Lys
        100                 105                 110 aaa aca cct gta tta cca gtt act cct att ctg agc cct tcc ttt tca    384
Lys Thr Pro Val Leu Pro Val Thr Pro Ile Leu Ser Pro Ser Phe Ser
        115                 120                 125 gca cag ctc tat ttt aga cct act att cag aga gga cag tgg cca cct    432
Ala Gln Leu Tyr Phe Arg Pro Thr Ile Gln Arg Gly Gln Trp Pro Pro
130                 135                 140 gga tta cct ggg cct tcc act tat gct tta cct tct att tat cct tct    480
Gly Leu Pro Gly Pro Ser Thr Tyr Ala Leu Pro Ser Ile Tyr Pro Ser
145                 150                 155                 160 act tac agt aaa cag gct gca ttc caa aat ggc ttc aat cca aga atg    528
Thr Tyr Ser Lys Gln Ala Ala Phe Gln Asn Gly Phe Asn Pro Arg Met
            165                 170                 175 ccc act ttt cca tct aca gaa cct ata tat tta agt ctt ccg gga caa    576
Pro Thr Phe Pro Ser Thr Glu Pro Ile Tyr Leu Ser Leu Pro Gly Gln
        180                 185                 190 tct cca tat ttc tca tat cct ttg aca cct gcc aca ccc ttt cat cca    624
Ser Pro Tyr Phe Ser Tyr Pro Leu Thr Pro Ala Thr Pro Phe His Pro
        195                 200                 205 caa gga agc tta cct atc tat cgt cca gta gtc agt act gac atg gca    672
Gln Gly Ser Leu Pro Ile Tyr Arg Pro Val Val Ser Thr Asp Met Ala
    210                 215                 220 aaa cta ttt gac aaa ata gct agt aca tca gaa ttt tta aaa aat ggg    720
Lys Leu Phe Asp Lys Ile Ala Ser Thr Ser Glu Phe Leu Lys Asn Gly
225                 230                 235                 240 aaa gca agg act gat ttg gag ata aca gat tca aaa gtc agc aat cta    768
Lys Ala Arg Thr Asp Leu Glu Ile Thr Asp Ser Lys Val Ser Asn Leu
            245                 250                 255 cag gta tct cca aag tct gag gat atc agt aaa ttt gac tgg tta gac    816
Gln Val Ser Pro Lys Ser Glu Asp Ile Ser Lys Phe Asp Trp Leu Asp
        260                 265                 270 ttg gat cct cta agt aag cct aag gtg gat aat gtg gag gta tta gac    864
Leu Asp Pro Leu Ser Lys Pro Lys Val Asp Asn Val Glu Val Leu Asp
        275                 280                 285 cat gag gaa gag aaa aat gtt tca agt ttg cta gca aag gat cct tgg    912
His Glu Glu Glu Lys Asn Val Ser Ser Leu Leu Ala Lys Asp Pro Trp
    290                 295                 300 gat gct gtt ctt ctt gaa gag aga tcg aca gca aat tgt cat ctt gaa    960
Asp Ala Val Leu Leu Glu Glu Arg Ser Thr Ala Asn Cys His Leu Glu
```

|     |     |     |     |     |     |     |     |     |     |     |     |      |
|-----|-----|-----|-----|-----|-----|-----|-----|-----|-----|-----|-----|------|
| 305 |     |     |     | 310 |     |     |     | 315 |     |     |     | 320  |
| aga | aag | gtg | aat | gga | aaa | tcc | ctt | tct | gtg | gca | act | gtt aca aga agc | 1008 |
| Arg | Lys | Val | Asn | Gly | Lys | Ser | Leu | Ser | Val | Ala | Thr | Val Thr Arg Ser |      |
|     |     |     |     | 325 |     |     |     | 330 |     |     |     | 335  |

```
      cag tct tta aat att cga aca act cag ctt gca aaa gcc cag ggc cat   1056
      Gln Ser Leu Asn Ile Arg Thr Thr Gln Leu Ala Lys Ala Gln Gly His
                      340                 345                 350 ata tct cag aaa gac cca aat ggg acc agt agt ttg cca act gga agt   1104
      Ile Ser Gln Lys Asp Pro Asn Gly Thr Ser Ser Leu Pro Thr Gly Ser
                      355                 360                 365 tct ctt ctt caa gaa gtt gaa gta cag aat gag gag atg gca gct ttt   1152
      Ser Leu Leu Gln Glu Val Glu Val Gln Asn Glu Glu Met Ala Ala Phe
                      370                 375                 380 tgt cga tcc att aca aaa ttg aag acc aaa ttt cca tat acc aat cac   1200
      Cys Arg Ser Ile Thr Lys Leu Lys Thr Lys Phe Pro Tyr Thr Asn His
      385                 390                 395                 400 cgc aca aac cca ggc tat ttg tta agt cca gtc aca gcg caa aga aac   1248
      Arg Thr Asn Pro Gly Tyr Leu Leu Ser Pro Val Thr Ala Gln Arg Asn
                      405                 410                 415 ata tgc gga gaa aat gct agt gtg aag gtc tcc att gac att gaa gga   1296
      Ile Cys Gly Glu Asn Ala Ser Val Lys Val Ser Ile Asp Ile Glu Gly
                      420                 425                 430 ttt cag cta cca gtt act ttt acg tgt gat gtg agt tct act gta gaa   1344
      Phe Gln Leu Pro Val Thr Phe Thr Cys Asp Val Ser Ser Thr Val Glu
                      435                 440                 445 atc att ata atg caa gcc ctt tgc tgg gta cat gat gac ttg aat caa   1392
      Ile Ile Ile Met Gln Ala Leu Cys Trp Val His Asp Asp Leu Asn Gln
                      450                 455                 460 gta gat gtt ggc agc tat gtt cta aaa gtt tgt ggt caa gag gaa gtg   1440
      Val Asp Val Gly Ser Tyr Val Leu Lys Val Cys Gly Gln Glu Glu Val
      465                 470                 475                 480 ctg cag aat aat cat tgc ctt gga agt cat gag cat att caa aac tgt   1488
      Leu Gln Asn Asn His Cys Leu Gly Ser His Glu His Ile Gln Asn Cys
                      485                 490                 495 cga aaa tgg gac aca gaa att aga cta caa ctc ttg acc ttc agt gca   1536
      Arg Lys Trp Asp Thr Glu Ile Arg Leu Gln Leu Leu Thr Phe Ser Ala
                      500                 505                 510 atg tgt caa aat ctg gcc cga aca gca gaa gat gat gaa aca ccc gtg   1584
      Met Cys Gln Asn Leu Ala Arg Thr Ala Glu Asp Asp Glu Thr Pro Val
                      515                 520                 525 gat tta aac aaa cac ctg tat caa ata gaa aaa cct tgc aaa gaa gcc   1632
      Asp Leu Asn Lys His Leu Tyr Gln Ile Glu Lys Pro Cys Lys Glu Ala
                      530                 535                 540 atg acg aga cac cct gtt gaa gaa ctc tta gat tct tat cac aac caa   1680
      Met Thr Arg His Pro Val Glu Glu Leu Leu Asp Ser Tyr His Asn Gln
      545                 550                 555                 560 gta gaa ctg gct ctt caa att gaa aac caa cac cga gca gta gat caa   1728
      Val Glu Leu Ala Leu Gln Ile Glu Asn Gln His Arg Ala Val Asp Gln
                      565                 570                 575 gta att aaa gct gta aga aaa atc tgt agt gct tta gat ggt gtc gag   1776
      Val Ile Lys Ala Val Arg Lys Ile Cys Ser Ala Leu Asp Gly Val Glu
                      580                 585                 590 act ctt gcc att aca gaa tca gta aag aag cta aag aga gca gtt aat   1824
      Thr Leu Ala Ile Thr Glu Ser Val Lys Lys Leu Lys Arg Ala Val Asn
                      595                 600                 605 ctt cca agg agt aaa act gct gat gtg act tct ttg ttt gga gga gaa   1872
      Leu Pro Arg Ser Lys Thr Ala Asp Val Thr Ser Leu Phe Gly Gly Glu
                      610                 615                 620 gac act agc agg agt tca act agg ggc tca ctt aat cct gaa aat cct   1920
```

```
Asp Thr Ser Arg Ser Ser Thr Arg Gly Ser Leu Asn Pro Glu Asn Pro
625                 630                 635                 640 gtt caa gta agc ata aac caa tta act gca gca att tat gat ctt ctc    1968
Val Gln Val Ser Ile Asn Gln Leu Thr Ala Ala Ile Tyr Asp Leu Leu
                645                 650                 655 aga ctc cat gca aat tct ggt agg agt cct aca gac tgt gcc caa agt    2016
Arg Leu His Ala Asn Ser Gly Arg Ser Pro Thr Asp Cys Ala Gln Ser
            660                 665                 670 agc aag agt gtc aag gaa gca tgg act aca aca gag cag ctc cag ttt    2064
Ser Lys Ser Val Lys Glu Ala Trp Thr Thr Thr Glu Gln Leu Gln Phe
        675                 680                 685 act att ttt gct gct cat gga att tca agt aat tgg gta tca aat tat    2112
Thr Ile Phe Ala Ala His Gly Ile Ser Ser Asn Trp Val Ser Asn Tyr
690                 695                 700 gaa aaa tac tac ttg ata tgt tca ctg tct cac aat gga aag gat ctt    2160
Glu Lys Tyr Tyr Leu Ile Cys Ser Leu Ser His Asn Gly Lys Asp Leu
705                 710                 715                 720 ttt aaa cct att caa tca aag aag gtt ggc act tac aag aat ttc ttc    2208
Phe Lys Pro Ile Gln Ser Lys Lys Val Gly Thr Tyr Lys Asn Phe Phe
                725                 730                 735 tat ctt att aaa tgg gat gaa cta atc att ttt cct atc cag ata tca    2256
Tyr Leu Ile Lys Trp Asp Glu Leu Ile Ile Phe Pro Ile Gln Ile Ser
            740                 745                 750 caa ttg cca tta gaa tca gtt ctt cac ctt act ctt ttt gga att tta    2304
Gln Leu Pro Leu Glu Ser Val Leu His Leu Thr Leu Phe Gly Ile Leu
        755                 760                 765 aat cag agc agt gga agt tcc cct gat tct aat aag cag aga aag gga    2352
Asn Gln Ser Ser Gly Ser Ser Pro Asp Ser Asn Lys Gln Arg Lys Gly
770                 775                 780 cca gaa gct ttg ggc aaa gtt tct tta cct ctt tgt gac ttt aga cgg    2400
Pro Glu Ala Leu Gly Lys Val Ser Leu Pro Leu Cys Asp Phe Arg Arg
785                 790                 795                 800 ttt tta aca tgt gga act aaa ctt cta tat ctt tgg act tca tca cat    2448
Phe Leu Thr Cys Gly Thr Lys Leu Leu Tyr Leu Trp Thr Ser Ser His
                805                 810                 815 aca aat tct gtt cct gga aca gtt acc aaa aaa gga tat gtc atg gaa    2496
Thr Asn Ser Val Pro Gly Thr Val Thr Lys Lys Gly Tyr Val Met Glu
            820                 825                 830 aga ata gtg cta cag gtt gat ttt cct tct cct gca ttt gat att att    2544
Arg Ile Val Leu Gln Val Asp Phe Pro Ser Pro Ala Phe Asp Ile Ile
        835                 840                 845 tat aca act cct caa gtt gac aga agc att ata cag caa cat aac tta    2592
Tyr Thr Thr Pro Gln Val Asp Arg Ser Ile Ile Gln Gln His Asn Leu
850                 855                 860 gaa aca cta gag aat gat ata aaa ggg aaa ctt ctt gat att ctt cat    2640
Glu Thr Leu Glu Asn Asp Ile Lys Gly Lys Leu Leu Asp Ile Leu His
865                 870                 875                 880 aaa gac tca tca ctt gga ctt tct aaa gaa gat aaa gct ttt tta tgg    2688
Lys Asp Ser Ser Leu Gly Leu Ser Lys Glu Asp Lys Ala Phe Leu Trp
                885                 890                 895 gag aaa cgt tat tat tgc ttc aaa cac cca aat tgt ctt cct aaa ata    2736
Glu Lys Arg Tyr Tyr Cys Phe Lys His Pro Asn Cys Leu Pro Lys Ile
            900                 905                 910 tta gca agc gcc cca aac tgg aaa tgg ggt aat ctt gcc aaa act tac    2784
Leu Ala Ser Ala Pro Asn Trp Lys Trp Gly Asn Leu Ala Lys Thr Tyr
        915                 920                 925 tca ttg ctt cac cag tgg cct gca ttg tac cca cta att gca ttg gaa    2832
Ser Leu Leu His Gln Trp Pro Ala Leu Tyr Pro Leu Ile Ala Leu Glu
930                 935                 940
```

-continued

| | | |
|---|---|---|
| ctt ctt gat tca aaa ttt gct gat cag gaa gta aga tcc cta gct gtg<br>Leu Leu Asp Ser Lys Phe Ala Asp Gln Glu Val Arg Ser Leu Ala Val<br>945                      950                      955                      960 | 2880 |
| acc tgg att gag gcc att agt gat gat gag cta aca gat ctt ctt cca<br>Thr Trp Ile Glu Ala Ile Ser Asp Asp Glu Leu Thr Asp Leu Leu Pro<br>                      965                      970                      975 | 2928 |
| cag ttt gta caa gct ttg aaa tat gaa att tac ttg aat agt tca tta<br>Gln Phe Val Gln Ala Leu Lys Tyr Glu Ile Tyr Leu Asn Ser Ser Leu<br>                      980                      985                      990 | 2976 |
| gtg caa ttc ctt ttg tcc agg gca ttg gga aat atc cag ata gca cac<br>Val Gln Phe Leu Leu Ser Arg Ala Leu Gly Asn Ile Gln Ile Ala His<br>      995                      1000                      1005 | 3024 |
| aat tta tat tgg ctt ctc aaa gat gcc ctg cat gat gta cag ttt<br>Asn Leu Tyr Trp Leu Leu Lys Asp Ala Leu His Asp Val Gln Phe<br>1010                      1015                      1020 | 3069 |
| agt acc cga tac gaa cat gtt ttg ggt gct ctc ctg tca gta gga<br>Ser Thr Arg Tyr Glu His Val Leu Gly Ala Leu Leu Ser Val Gly<br>          1025                      1030                      1035 | 3114 |
| gga aaa cga ctt aga gaa gaa ctt cta aaa cag acg aaa ctt gta<br>Gly Lys Arg Leu Arg Glu Glu Leu Leu Lys Gln Thr Lys Leu Val<br>1040                      1045                      1050 | 3159 |
| cag ctt tta gga gga gta gca gaa aaa gta agg cag gct agt gga<br>Gln Leu Leu Gly Gly Val Ala Glu Lys Val Arg Gln Ala Ser Gly<br>          1055                      1060                      1065 | 3204 |
| tca gcc aga cag gtt gtt ctc caa aga agt atg gaa cga gta cag<br>Ser Ala Arg Gln Val Val Leu Gln Arg Ser Met Glu Arg Val Gln<br>1070                      1075                      1080 | 3249 |
| tcc ttt ttt cag aaa aat aaa tgc cgt ctc cct ctc aag cca agt<br>Ser Phe Phe Gln Lys Asn Lys Cys Arg Leu Pro Leu Lys Pro Ser<br>          1085                      1090                      1095 | 3294 |
| cta gtg gca aaa gaa tta aat att aag tcg tgt tcc ttc ttc agt<br>Leu Val Ala Lys Glu Leu Asn Ile Lys Ser Cys Ser Phe Phe Ser<br>1100                      1105                      1110 | 3339 |
| tct aat gct gtc ccc cta aaa gtc aca atg gtg aat gct gac cct<br>Ser Asn Ala Val Pro Leu Lys Val Thr Met Val Asn Ala Asp Pro<br>          1115                      1120                      1125 | 3384 |
| ctg gga gaa gaa att aat gtc atg ttt aag gtt ggt gaa gat ctt<br>Leu Gly Glu Glu Ile Asn Val Met Phe Lys Val Gly Glu Asp Leu<br>1130                      1135                      1140 | 3429 |
| cgg caa gat atg tta gct tta cag atg ata aag att atg gat aag<br>Arg Gln Asp Met Leu Ala Leu Gln Met Ile Lys Ile Met Asp Lys<br>          1145                      1150                      1155 | 3474 |
| atc tgg ctt aaa gaa gga cta gat ctg agg atg gta att ttc aaa<br>Ile Trp Leu Lys Glu Gly Leu Asp Leu Arg Met Val Ile Phe Lys<br>1160                      1165                      1170 | 3519 |
| tgt ctc tca act ggc aga gat cga ggc atg gtg gag ctg gtt cct<br>Cys Leu Ser Thr Gly Arg Asp Arg Gly Met Val Glu Leu Val Pro<br>          1175                      1180                      1185 | 3564 |
| gct tcc gat acc ctc agg aaa atc caa gtg gaa tat ggt gtg aca<br>Ala Ser Asp Thr Leu Arg Lys Ile Gln Val Glu Tyr Gly Val Thr<br>1190                      1195                      1200 | 3609 |
| gga tcc ttt aaa gat aaa cca ctt gca gag tgg cta agg aaa tac<br>Gly Ser Phe Lys Asp Lys Pro Leu Ala Glu Trp Leu Arg Lys Tyr<br>          1205                      1210                      1215 | 3654 |
| aat ccc tct gaa gaa gaa tat gaa aag gct tca gag aac ttt atc<br>Asn Pro Ser Glu Glu Glu Tyr Glu Lys Ala Ser Glu Asn Phe Ile<br>1220                      1225                      1230 | 3699 |
| tat tcc tgt gct gga tgc tgt gta gcc acc tat gtt tta ggc atc<br>Tyr Ser Cys Ala Gly Cys Cys Val Ala Thr Tyr Val Leu Gly Ile<br>          1235                      1240                      1245 | 3744 |

-continued

| | | | | | | | | | | | | | | |
|---|---|---|---|---|---|---|---|---|---|---|---|---|---|---|
| tgt | gat | cga | cac | aat | gac | aat | ata | atg | ctt | cga | agc | acg | gga | cac | 3789 |
| Cys | Asp | Arg | His | Asn | Asp | Asn | Ile | Met | Leu | Arg | Ser | Thr | Gly | His | |
| 1250 | | | | 1255 | | | | | 1260 | | | | | | |

| atg | ttt | cac | att | gac | ttt | gga | aag | ttt | ttg | gga | cat | gca | cag | atg | 3834 |
|---|---|---|---|---|---|---|---|---|---|---|---|---|---|---|---|
| Met | Phe | His | Ile | Asp | Phe | Gly | Lys | Phe | Leu | Gly | His | Ala | Gln | Met | |
| 1265 | | | | 1270 | | | | | 1275 | | | | | | |

| ttt | ggc | agc | ttc | aaa | agg | gat | cgg | gct | cct | ttt | gtg | ctg | acc | tct | 3879 |
|---|---|---|---|---|---|---|---|---|---|---|---|---|---|---|---|
| Phe | Gly | Ser | Phe | Lys | Arg | Asp | Arg | Ala | Pro | Phe | Val | Leu | Thr | Ser | |
| 1280 | | | | 1285 | | | | | 1290 | | | | | | |

| gat | atg | gca | tat | gtc | att | aat | ggg | ggt | gaa | aag | ccc | acc | att | cgt | 3924 |
|---|---|---|---|---|---|---|---|---|---|---|---|---|---|---|---|
| Asp | Met | Ala | Tyr | Val | Ile | Asn | Gly | Gly | Glu | Lys | Pro | Thr | Ile | Arg | |
| 1295 | | | | 1300 | | | | | 1305 | | | | | | |

| ttt | cag | ttg | ttt | gtg | gac | ctc | tgc | tgt | cag | gcc | tac | aac | ttg | ata | 3969 |
|---|---|---|---|---|---|---|---|---|---|---|---|---|---|---|---|
| Phe | Gln | Leu | Phe | Val | Asp | Leu | Cys | Cys | Gln | Ala | Tyr | Asn | Leu | Ile | |
| 1310 | | | | 1315 | | | | | 1320 | | | | | | |

| aga | aag | cag | aca | aac | ctt | ttt | ctt | aac | ctc | ctt | tca | ctg | atg | att | 4014 |
|---|---|---|---|---|---|---|---|---|---|---|---|---|---|---|---|
| Arg | Lys | Gln | Thr | Asn | Leu | Phe | Leu | Asn | Leu | Leu | Ser | Leu | Met | Ile | |
| 1325 | | | | 1330 | | | | | 1335 | | | | | | |

| cct | tca | ggg | tta | cca | gaa | ctt | aca | agt | att | caa | gat | ttg | aaa | tac | 4059 |
|---|---|---|---|---|---|---|---|---|---|---|---|---|---|---|---|
| Pro | Ser | Gly | Leu | Pro | Glu | Leu | Thr | Ser | Ile | Gln | Asp | Leu | Lys | Tyr | |
| 1340 | | | | 1345 | | | | | 1350 | | | | | | |

| gtt | aga | gat | gca | ctt | caa | ccc | caa | act | aca | gac | gca | gaa | gct | aca | 4104 |
|---|---|---|---|---|---|---|---|---|---|---|---|---|---|---|---|
| Val | Arg | Asp | Ala | Leu | Gln | Pro | Gln | Thr | Thr | Asp | Ala | Glu | Ala | Thr | |
| 1355 | | | | 1360 | | | | | 1365 | | | | | | |

| att | ttc | ttt | act | agg | ctt | att | gaa | tca | agt | ttg | gga | agc | att | gcc | 4149 |
|---|---|---|---|---|---|---|---|---|---|---|---|---|---|---|---|
| Ile | Phe | Phe | Thr | Arg | Leu | Ile | Glu | Ser | Ser | Leu | Gly | Ser | Ile | Ala | |
| 1370 | | | | 1375 | | | | | 1380 | | | | | | |

| aca | aag | ttt | aac | ttc | ttc | att | cac | aac | ctt | gct | cag | ctt | cgt | ttt | 4194 |
|---|---|---|---|---|---|---|---|---|---|---|---|---|---|---|---|
| Thr | Lys | Phe | Asn | Phe | Phe | Ile | His | Asn | Leu | Ala | Gln | Leu | Arg | Phe | |
| 1385 | | | | 1390 | | | | | 1395 | | | | | | |

| tct | ggt | ctt | cct | tct | aat | gat | gag | ccc | atc | ctt | tca | ttt | tca | cct | 4239 |
|---|---|---|---|---|---|---|---|---|---|---|---|---|---|---|---|
| Ser | Gly | Leu | Pro | Ser | Asn | Asp | Glu | Pro | Ile | Leu | Ser | Phe | Ser | Pro | |
| 1400 | | | | 1405 | | | | | 1410 | | | | | | |

| aaa | aca | tac | tcc | ttt | aga | caa | gat | ggt | cga | atc | aag | gaa | gtc | tct | 4284 |
|---|---|---|---|---|---|---|---|---|---|---|---|---|---|---|---|
| Lys | Thr | Tyr | Ser | Phe | Arg | Gln | Asp | Gly | Arg | Ile | Lys | Glu | Val | Ser | |
| 1415 | | | | 1420 | | | | | 1425 | | | | | | |

| gtt | ttt | aca | tat | cat | aag | aaa | tac | aac | cca | gat | aaa | cat | tat | att | 4329 |
|---|---|---|---|---|---|---|---|---|---|---|---|---|---|---|---|
| Val | Phe | Thr | Tyr | His | Lys | Lys | Tyr | Asn | Pro | Asp | Lys | His | Tyr | Ile | |
| 1430 | | | | 1435 | | | | | 1440 | | | | | | |

| tat | gta | gtc | cga | att | ttg | tgg | gaa | gga | cag | att | gaa | cca | tca | ttt | 4374 |
|---|---|---|---|---|---|---|---|---|---|---|---|---|---|---|---|
| Tyr | Val | Val | Arg | Ile | Leu | Trp | Glu | Gly | Gln | Ile | Glu | Pro | Ser | Phe | |
| 1445 | | | | 1450 | | | | | 1455 | | | | | | |

| gtc | ttc | cga | aca | ttt | gtc | gaa | ttt | cag | gaa | ctt | cac | aat | aag | ctc | 4419 |
|---|---|---|---|---|---|---|---|---|---|---|---|---|---|---|---|
| Val | Phe | Arg | Thr | Phe | Val | Glu | Phe | Gln | Glu | Leu | His | Asn | Lys | Leu | |
| 1460 | | | | 1465 | | | | | 1470 | | | | | | |

| agt | att | att | ttt | cca | ctt | tgg | aag | tta | cca | ggc | ttt | cct | aat | agg | 4464 |
|---|---|---|---|---|---|---|---|---|---|---|---|---|---|---|---|
| Ser | Ile | Ile | Phe | Pro | Leu | Trp | Lys | Leu | Pro | Gly | Phe | Pro | Asn | Arg | |
| 1475 | | | | 1480 | | | | | 1485 | | | | | | |

| atg | gtt | cta | gga | aga | aca | cac | ata | aaa | gat | gta | gca | gcc | aaa | agg | 4509 |
|---|---|---|---|---|---|---|---|---|---|---|---|---|---|---|---|
| Met | Val | Leu | Gly | Arg | Thr | His | Ile | Lys | Asp | Val | Ala | Ala | Lys | Arg | |
| 1490 | | | | 1495 | | | | | 1500 | | | | | | |

| aaa | att | gag | tta | aac | agt | tac | tta | cag | agt | ttg | atg | aat | gct | tca | 4554 |
|---|---|---|---|---|---|---|---|---|---|---|---|---|---|---|---|
| Lys | Ile | Glu | Leu | Asn | Ser | Tyr | Leu | Gln | Ser | Leu | Met | Asn | Ala | Ser | |
| 1505 | | | | 1510 | | | | | 1515 | | | | | | |

| acg | gat | gta | gca | gag | tgt | gat | ctt | gtt | tgt | act | ttc | ttc | cac | cct | 4599 |
|---|---|---|---|---|---|---|---|---|---|---|---|---|---|---|---|
| Thr | Asp | Val | Ala | Glu | Cys | Asp | Leu | Val | Cys | Thr | Phe | Phe | His | Pro | |
| 1520 | | | | 1525 | | | | | 1530 | | | | | | |

| tta | ctt | cgt | gat | gag | aaa | gct | gaa | ggg | ata | gct | agg | tct | gca | gat | 4644 |
|---|---|---|---|---|---|---|---|---|---|---|---|---|---|---|---|
| Leu | Leu | Arg | Asp | Glu | Lys | Ala | Glu | Gly | Ile | Ala | Arg | Ser | Ala | Asp | |

|  |  |  |  |  |  |  |  |  |  |  |
|---|---|---|---|---|---|---|---|---|---|---|
| gca | ggt | tcc | ttc | agt | cct | act | cca | ggc | caa | ata | gga | gga | gct | gtg | 4689 |
| Ala | Gly | Ser | Phe | Ser | Pro | Thr | Pro | Gly | Gln | Ile | Gly | Gly | Ala | Val |
| 1550 |  |  |  | 1555 |  |  |  | 1560 |  |  |

```
gca ggt tcc ttc agt cct act cca ggc caa ata gga gga gct gtg      4689
Ala Gly Ser Phe Ser Pro Thr Pro Gly Gln Ile Gly Gly Ala Val
    1550                1555                1560 aaa tta tcc atc tct tac cga aat ggt act ctt ttc atc atg gtg      4734
Lys Leu Ser Ile Ser Tyr Arg Asn Gly Thr Leu Phe Ile Met Val
1565                1570                1575 atg cat atc aaa gat ctt gtt act gaa gat gga gct gac cca aat      4779
Met His Ile Lys Asp Leu Val Thr Glu Asp Gly Ala Asp Pro Asn
    1580                1585                1590 cca tat gtc aaa aca tac cta ctt cca gat aac cac aaa aca tcc      4824
Pro Tyr Val Lys Thr Tyr Leu Leu Pro Asp Asn His Lys Thr Ser
1595                1600                1605 aaa cgt aaa acc aaa att tca cga aaa acg agg aat ccg aca ttc      4869
Lys Arg Lys Thr Lys Ile Ser Arg Lys Thr Arg Asn Pro Thr Phe
    1610                1615                1620 aat gaa atg ctt gta tac agt gga tat agc aaa gaa acc cta aga      4914
Asn Glu Met Leu Val Tyr Ser Gly Tyr Ser Lys Glu Thr Leu Arg
1625                1630                1635 cag cga gaa ctt caa cta agt gta ctc agt gca gaa tct ctg cgg      4959
Gln Arg Glu Leu Gln Leu Ser Val Leu Ser Ala Glu Ser Leu Arg
    1640                1645                1650 gag aat ttt ttc ttg ggt gga gta acc ctg cct ttg aaa gat ttc      5004
Glu Asn Phe Phe Leu Gly Gly Val Thr Leu Pro Leu Lys Asp Phe
1655                1660                1665 aac ttg agc aaa gag acg gtt aaa tgg tat cag ctg act gcg gca      5049
Asn Leu Ser Lys Glu Thr Val Lys Trp Tyr Gln Leu Thr Ala Ala
    1670                1675                1680 aca tac ttg taa                                                   5061
Thr Tyr Leu
    1685
```

<210> SEQ ID NO 2
<211> LENGTH: 1686
<212> TYPE: PRT
<213> ORGANISM: Homo sapiens

<400> SEQUENCE: 2

```
Met Ala Gln Ile Phe Ser Asn Ser Gly Phe Lys Glu Cys Pro Phe Ser
1               5                   10                  15

His Pro Glu Pro Thr Arg Ala Lys Asp Val Asp Lys Glu Ala Leu
            20                  25                  30

Gln Met Glu Ala Glu Ala Leu Ala Lys Leu Gln Lys Asp Arg Gln Val
        35                  40                  45

Thr Asp Asn Gln Arg Gly Phe Glu Leu Ser Ser Thr Arg Lys Lys
    50                  55                  60

Ala Gln Val Tyr Asn Lys Gln Asp Tyr Asp Leu Met Val Phe Pro Glu
65                  70                  75                  80

Ser Asp Ser Gln Lys Arg Ala Leu Asp Ile Asp Val Glu Lys Leu Thr
                85                  90                  95

Gln Ala Glu Leu Glu Lys Leu Leu Leu Asp Asp Ser Phe Glu Thr Lys
            100                 105                 110

Lys Thr Pro Val Leu Pro Val Thr Pro Ile Leu Ser Pro Ser Phe Ser
        115                 120                 125

Ala Gln Leu Tyr Phe Arg Pro Thr Ile Gln Arg Gly Gln Trp Pro Pro
    130                 135                 140

Gly Leu Pro Gly Pro Ser Thr Tyr Ala Leu Pro Ser Ile Tyr Pro Ser
145                 150                 155                 160
```

```
Thr Tyr Ser Lys Gln Ala Ala Phe Gln Asn Gly Phe Asn Pro Arg Met
            165                 170                 175

Pro Thr Phe Pro Ser Thr Glu Pro Ile Tyr Leu Ser Leu Pro Gly Gln
        180                 185                 190

Ser Pro Tyr Phe Ser Tyr Pro Leu Thr Pro Ala Thr Pro Phe His Pro
        195                 200                 205

Gln Gly Ser Leu Pro Ile Tyr Arg Pro Val Val Ser Thr Asp Met Ala
        210                 215                 220

Lys Leu Phe Asp Lys Ile Ala Ser Thr Ser Glu Phe Leu Lys Asn Gly
225                 230                 235                 240

Lys Ala Arg Thr Asp Leu Glu Ile Thr Asp Ser Lys Val Ser Asn Leu
            245                 250                 255

Gln Val Ser Pro Lys Ser Glu Asp Ile Ser Lys Phe Asp Trp Leu Asp
            260                 265                 270

Leu Asp Pro Leu Ser Lys Pro Lys Val Asp Asn Val Glu Val Leu Asp
            275                 280                 285

His Glu Glu Lys Asn Val Ser Ser Leu Leu Ala Lys Asp Pro Trp
            290                 295                 300

Asp Ala Val Leu Leu Glu Glu Arg Ser Thr Ala Asn Cys His Leu Glu
305                 310                 315                 320

Arg Lys Val Asn Gly Lys Ser Leu Ser Val Ala Thr Val Thr Arg Ser
            325                 330                 335

Gln Ser Leu Asn Ile Arg Thr Thr Gln Leu Ala Lys Ala Gln Gly His
            340                 345                 350

Ile Ser Gln Lys Asp Pro Asn Gly Thr Ser Ser Leu Pro Thr Gly Ser
            355                 360                 365

Ser Leu Leu Gln Glu Val Glu Val Gln Asn Glu Glu Met Ala Ala Phe
            370                 375                 380

Cys Arg Ser Ile Thr Lys Leu Lys Thr Lys Phe Pro Tyr Thr Asn His
385                 390                 395                 400

Arg Thr Asn Pro Gly Tyr Leu Leu Ser Pro Val Thr Ala Gln Arg Asn
            405                 410                 415

Ile Cys Gly Glu Asn Ala Ser Val Lys Val Ser Ile Asp Ile Glu Gly
            420                 425                 430

Phe Gln Leu Pro Val Thr Phe Thr Cys Asp Val Ser Ser Thr Val Glu
            435                 440                 445

Ile Ile Ile Met Gln Ala Leu Cys Trp Val His Asp Asp Leu Asn Gln
            450                 455                 460

Val Asp Val Gly Ser Tyr Val Leu Lys Val Cys Gly Gln Glu Glu Val
465                 470                 475                 480

Leu Gln Asn Asn His Cys Leu Gly Ser His Glu His Ile Gln Asn Cys
            485                 490                 495

Arg Lys Trp Asp Thr Glu Ile Arg Leu Gln Leu Thr Phe Ser Ala
            500                 505                 510

Met Cys Gln Asn Leu Ala Arg Thr Ala Glu Asp Glu Thr Pro Val
            515                 520                 525

Asp Leu Asn Lys His Leu Tyr Gln Ile Glu Lys Pro Cys Lys Glu Ala
530                 535                 540

Met Thr Arg His Pro Val Glu Glu Leu Leu Asp Ser Tyr His Asn Gln
545                 550                 555                 560

Val Glu Leu Ala Leu Gln Ile Glu Asn Gln His Arg Ala Val Asp Gln
            565                 570                 575
```

-continued

Val Ile Lys Ala Val Arg Lys Ile Cys Ser Ala Leu Asp Gly Val Glu
        580                 585                 590

Thr Leu Ala Ile Thr Glu Ser Val Lys Lys Leu Lys Arg Ala Val Asn
        595                 600                 605

Leu Pro Arg Ser Lys Thr Ala Asp Val Thr Ser Leu Phe Gly Gly Glu
        610                 615                 620

Asp Thr Ser Arg Ser Ser Thr Arg Gly Ser Leu Asn Pro Glu Asn Pro
625                 630                 635                 640

Val Gln Val Ser Ile Asn Gln Leu Thr Ala Ala Ile Tyr Asp Leu Leu
                645                 650                 655

Arg Leu His Ala Asn Ser Gly Arg Ser Pro Thr Asp Cys Ala Gln Ser
        660                 665                 670

Ser Lys Ser Val Lys Glu Ala Trp Thr Thr Thr Glu Gln Leu Gln Phe
        675                 680                 685

Thr Ile Phe Ala Ala His Gly Ile Ser Ser Asn Trp Val Ser Asn Tyr
        690                 695                 700

Glu Lys Tyr Tyr Leu Ile Cys Ser Leu Ser His Asn Gly Lys Asp Leu
705                 710                 715                 720

Phe Lys Pro Ile Gln Ser Lys Val Gly Thr Tyr Lys Asn Phe Phe
                725                 730                 735

Tyr Leu Ile Lys Trp Asp Glu Leu Ile Ile Phe Pro Ile Gln Ile Ser
        740                 745                 750

Gln Leu Pro Leu Glu Ser Val Leu His Leu Thr Leu Phe Gly Ile Leu
        755                 760                 765

Asn Gln Ser Ser Gly Ser Ser Pro Asp Ser Asn Lys Gln Arg Lys Gly
        770                 775                 780

Pro Glu Ala Leu Gly Lys Val Ser Leu Pro Leu Cys Asp Phe Arg Arg
785                 790                 795                 800

Phe Leu Thr Cys Gly Thr Lys Leu Leu Tyr Leu Trp Thr Ser Ser His
                805                 810                 815

Thr Asn Ser Val Pro Gly Thr Val Thr Lys Lys Gly Tyr Val Met Glu
        820                 825                 830

Arg Ile Val Leu Gln Val Asp Phe Pro Ser Pro Ala Phe Asp Ile Ile
        835                 840                 845

Tyr Thr Thr Pro Gln Val Asp Arg Ser Ile Ile Gln Gln His Asn Leu
        850                 855                 860

Glu Thr Leu Glu Asn Asp Ile Lys Gly Lys Leu Leu Asp Ile Leu His
865                 870                 875                 880

Lys Asp Ser Ser Leu Gly Leu Ser Lys Glu Asp Lys Ala Phe Leu Trp
                885                 890                 895

Glu Lys Arg Tyr Tyr Cys Phe Lys His Pro Asn Cys Leu Pro Lys Ile
        900                 905                 910

Leu Ala Ser Ala Pro Asn Trp Lys Trp Gly Asn Leu Ala Lys Thr Tyr
        915                 920                 925

Ser Leu Leu His Gln Trp Pro Ala Leu Tyr Pro Leu Ile Ala Leu Glu
        930                 935                 940

Leu Leu Asp Ser Lys Phe Ala Asp Gln Glu Val Arg Ser Leu Ala Val
945                 950                 955                 960

Thr Trp Ile Glu Ala Ile Ser Asp Glu Leu Thr Asp Leu Leu Pro
                965                 970                 975

Gln Phe Val Gln Ala Leu Lys Tyr Glu Ile Tyr Leu Asn Ser Ser Leu
        980                 985                 990

Val Gln Phe Leu Leu Ser Arg Ala  Leu Gly Asn Ile Gln  Ile Ala His

-continued

```
              995                 1000                1005
Asn  Leu  Tyr  Trp  Leu  Leu  Lys  Asp  Ala  Leu  His  Asp  Val  Gln  Phe
          1010                1015                1020

Ser  Thr  Arg  Tyr  Glu  His  Val  Leu  Gly  Ala  Leu  Leu  Ser  Val  Gly
          1025                1030                1035

Gly  Lys  Arg  Leu  Arg  Glu  Glu  Leu  Leu  Lys  Gln  Thr  Lys  Leu  Val
          1040                1045                1050

Gln  Leu  Leu  Gly  Gly  Val  Ala  Glu  Lys  Val  Arg  Gln  Ala  Ser  Gly
          1055                1060                1065

Ser  Ala  Arg  Gln  Val  Val  Leu  Gln  Arg  Ser  Met  Glu  Arg  Val  Gln
          1070                1075                1080

Ser  Phe  Phe  Gln  Lys  Asn  Lys  Cys  Arg  Leu  Pro  Leu  Lys  Pro  Ser
          1085                1090                1095

Leu  Val  Ala  Lys  Glu  Leu  Asn  Ile  Lys  Ser  Cys  Ser  Phe  Phe  Ser
          1100                1105                1110

Ser  Asn  Ala  Val  Pro  Leu  Lys  Val  Thr  Met  Val  Asn  Ala  Asp  Pro
          1115                1120                1125

Leu  Gly  Glu  Glu  Ile  Asn  Val  Met  Phe  Lys  Val  Gly  Glu  Asp  Leu
          1130                1135                1140

Arg  Gln  Asp  Met  Leu  Ala  Leu  Gln  Met  Ile  Lys  Ile  Met  Asp  Lys
          1145                1150                1155

Ile  Trp  Leu  Lys  Glu  Gly  Leu  Asp  Leu  Arg  Met  Val  Ile  Phe  Lys
          1160                1165                1170

Cys  Leu  Ser  Thr  Gly  Arg  Asp  Arg  Gly  Met  Val  Glu  Leu  Val  Pro
          1175                1180                1185

Ala  Ser  Asp  Thr  Leu  Arg  Lys  Ile  Gln  Val  Glu  Tyr  Gly  Val  Thr
          1190                1195                1200

Gly  Ser  Phe  Lys  Asp  Lys  Pro  Leu  Ala  Glu  Trp  Leu  Arg  Lys  Tyr
          1205                1210                1215

Asn  Pro  Ser  Glu  Glu  Glu  Tyr  Glu  Lys  Ala  Ser  Glu  Asn  Phe  Ile
          1220                1225                1230

Tyr  Ser  Cys  Ala  Gly  Cys  Cys  Val  Ala  Thr  Tyr  Val  Leu  Gly  Ile
          1235                1240                1245

Cys  Asp  Arg  His  Asn  Asp  Asn  Ile  Met  Leu  Arg  Ser  Thr  Gly  His
          1250                1255                1260

Met  Phe  His  Ile  Asp  Phe  Gly  Lys  Phe  Leu  Gly  His  Ala  Gln  Met
          1265                1270                1275

Phe  Gly  Ser  Phe  Lys  Arg  Asp  Arg  Ala  Pro  Phe  Val  Leu  Thr  Ser
          1280                1285                1290

Asp  Met  Ala  Tyr  Val  Ile  Asn  Gly  Gly  Glu  Lys  Pro  Thr  Ile  Arg
          1295                1300                1305

Phe  Gln  Leu  Phe  Val  Asp  Leu  Cys  Cys  Gln  Ala  Tyr  Asn  Leu  Ile
          1310                1315                1320

Arg  Lys  Gln  Thr  Asn  Leu  Phe  Leu  Asn  Leu  Leu  Ser  Leu  Met  Ile
          1325                1330                1335

Pro  Ser  Gly  Leu  Pro  Glu  Leu  Thr  Ser  Ile  Gln  Asp  Leu  Lys  Tyr
          1340                1345                1350

Val  Arg  Asp  Ala  Leu  Gln  Pro  Gln  Thr  Thr  Asp  Ala  Glu  Ala  Thr
          1355                1360                1365

Ile  Phe  Phe  Thr  Arg  Leu  Ile  Glu  Ser  Ser  Leu  Gly  Ser  Ile  Ala
          1370                1375                1380

Thr  Lys  Phe  Asn  Phe  Phe  Ile  His  Asn  Leu  Ala  Gln  Leu  Arg  Phe
          1385                1390                1395
```

-continued

```
Ser Gly Leu Pro Ser Asn Asp Glu Pro Ile Leu Ser Phe Ser Pro
    1400                1405                1410

Lys Thr Tyr Ser Phe Arg Gln Asp Gly Arg Ile Lys Glu Val Ser
    1415                1420                1425

Val Phe Thr Tyr His Lys Lys Tyr Asn Pro Asp Lys His Tyr Ile
    1430                1435                1440

Tyr Val Val Arg Ile Leu Trp Glu Gly Gln Ile Glu Pro Ser Phe
    1445                1450                1455

Val Phe Arg Thr Phe Val Glu Phe Gln Glu Leu His Asn Lys Leu
    1460                1465                1470

Ser Ile Ile Phe Pro Leu Trp Lys Leu Pro Gly Phe Pro Asn Arg
    1475                1480                1485

Met Val Leu Gly Arg Thr His Ile Lys Asp Val Ala Ala Lys Arg
    1490                1495                1500

Lys Ile Glu Leu Asn Ser Tyr Leu Gln Ser Leu Met Asn Ala Ser
    1505                1510                1515

Thr Asp Val Ala Glu Cys Asp Leu Val Cys Thr Phe Phe His Pro
    1520                1525                1530

Leu Leu Arg Asp Glu Lys Ala Glu Gly Ile Ala Arg Ser Ala Asp
    1535                1540                1545

Ala Gly Ser Phe Ser Pro Thr Pro Gly Gln Ile Gly Gly Ala Val
    1550                1555                1560

Lys Leu Ser Ile Ser Tyr Arg Asn Gly Thr Leu Phe Ile Met Val
    1565                1570                1575

Met His Ile Lys Asp Leu Val Thr Glu Asp Gly Ala Asp Pro Asn
    1580                1585                1590

Pro Tyr Val Lys Thr Tyr Leu Leu Pro Asp Asn His Lys Thr Ser
    1595                1600                1605

Lys Arg Lys Thr Lys Ile Ser Arg Lys Thr Arg Asn Pro Thr Phe
    1610                1615                1620

Asn Glu Met Leu Val Tyr Ser Gly Tyr Ser Lys Glu Thr Leu Arg
    1625                1630                1635

Gln Arg Glu Leu Gln Leu Ser Val Leu Ser Ala Glu Ser Leu Arg
    1640                1645                1650

Glu Asn Phe Phe Leu Gly Gly Val Thr Leu Pro Leu Lys Asp Phe
    1655                1660                1665

Asn Leu Ser Lys Glu Thr Val Lys Trp Tyr Gln Leu Thr Ala Ala
    1670                1675                1680

Thr Tyr Leu
    1685
```

<210> SEQ ID NO 3
<211> LENGTH: 27
<212> TYPE: DNA
<213> ORGANISM: Artificial Sequence
<220> FEATURE:
<223> OTHER INFORMATION: primer

<400> SEQUENCE: 3
ctcttcctca tggtctaata cctccac        27

<210> SEQ ID NO 4
<211> LENGTH: 20
<212> TYPE: DNA
<213> ORGANISM: Artificial Sequence
<220> FEATURE:

```
<223> OTHER INFORMATION: primer
<221> NAME/KEY: misc_feature
<222> LOCATION: (3)..(3)
<223> OTHER INFORMATION: n can be any nucleotide
<221> NAME/KEY: misc_feature
<222> LOCATION: (15)..(15)
<223> OTHER INFORMATION: n can be any nucleotide
<221> NAME/KEY: misc_feature
<222> LOCATION: (6)..(6)
<223> OTHER INFORMATION: n can be either T or C
<221> NAME/KEY: misc_feature
<222> LOCATION: (9)..(9)
<223> OTHER INFORMATION: n can be T or C
<221> NAME/KEY: misc_feature
<222> LOCATION: (10)..(10)
<223> OTHER INFORMATION: n can be either T or C.
<221> NAME/KEY: misc_feature
<222> LOCATION: (12)..(12)
<223> OTHER INFORMATION: n can be either A or G.
<221> NAME/KEY: misc_feature
<222> LOCATION: (18)..(18)
<223> OTHER INFORMATION: n can be either A or G.

<400> SEQUENCE: 4
ggngangann tncgncanga                                          20

<210> SEQ ID NO 5
<211> LENGTH: 27
<212> TYPE: DNA
<213> ORGANISM: Artificial Sequence
<220> FEATURE:
<223> OTHER INFORMATION: primer
<221> NAME/KEY: misc_feature
<222> LOCATION: (16)..(16)
<223> OTHER INFORMATION: n can be either A, G, or T.
<221> NAME/KEY: misc_feature
<222> LOCATION: (7)..(7)
<223> OTHER INFORMATION: n is an I.
<221> NAME/KEY: misc_feature
<222> LOCATION: (1)..(1)
<223> OTHER INFORMATION: n can be A or G.
<221> NAME/KEY: misc_feature
<222> LOCATION: (4)..(4)
<223> OTHER INFORMATION: n can be A or G..
<221> NAME/KEY: misc_feature
<222> LOCATION: (10)..(10)
<223> OTHER INFORMATION: n can be A or G.
<221> NAME/KEY: misc_feature
<222> LOCATION: (13)..(13)
<223> OTHER INFORMATION: n can be A or G.
<221> NAME/KEY: misc_feature
<222> LOCATION: (19)..(19)
<223> OTHER INFORMATION: n can be A or G.
<221> NAME/KEY: misc_feature
<222> LOCATION: (22)..(22)
<223> OTHER INFORMATION: n can be A or G.
<221> NAME/KEY: misc_feature
<222> LOCATION: (25)..(25)
<223> OTHER INFORMATION: n can be A or G.

<400> SEQUENCE: 5
naantgnccn aantcnatnt gntgnaa                                  27

<210> SEQ ID NO 6
<211> LENGTH: 27
<212> TYPE: DNA
<213> ORGANISM: Artificial Sequence
<220> FEATURE:
<223> OTHER INFORMATION: primer

<400> SEQUENCE: 6
tatctccaaa tcagtccttg ctttccc                                  27

<210> SEQ ID NO 7
```

-continued

```
<211> LENGTH: 147
<212> TYPE: PRT
<213> ORGANISM: Homo sapiens

<400> SEQUENCE: 7

Met Pro Thr Phe Pro Ser Thr Glu Ser Val Tyr Leu Arg Leu Pro Gly
1               5                   10                  15

Gln Ser Pro Tyr Phe Ser Tyr Pro Leu Thr Pro Ala Thr Pro Phe His
            20                  25                  30

Pro Gln Gly Ser Leu Pro Val Tyr Arg Pro Leu Val Ser Pro Asp Met
        35                  40                  45

Ala Lys Leu Phe Glu Lys Ile Ala Ser Thr Ser Glu Phe Leu Lys Asn
50                  55                  60

Gly Lys Ala Arg Thr Asp Leu Glu Ile Ala Asn Ser Lys Ala Ser Val
65                  70                  75                  80

Cys Asn Leu Gln Ile Ser Pro Lys Ser Glu Asp Ile Asn Lys Phe Asp
            85                  90                  95

Trp Leu Asp Leu Asp Pro Leu Ser Lys Pro Lys Val Asp Tyr Val Glu
        100                 105                 110

Val Leu Glu His Glu Glu Lys Lys Asp Pro Val Leu Leu Ala Glu
            115                 120                 125

Asp Pro Trp Asp Ala Val Leu Leu Glu Glu Arg Ser Pro Ser Cys His
        130                 135                 140

Leu Glu Arg
145

<210> SEQ ID NO 8
<211> LENGTH: 294
<212> TYPE: PRT
<213> ORGANISM: Homo sapiens

<400> SEQUENCE: 8

Met Ala Gln Ile Ser Asn Asn Ser Glu Phe Lys Gln Cys Ser Ser Ser
1               5                   10                  15

His Pro Glu Pro Ile Arg Thr Lys Asp Val Asn Lys Ala Glu Ala Leu
            20                  25                  30

Gln Met Glu Ala Glu Ala Leu Ala Lys Leu Gln Lys Asp Arg Gln Met
        35                  40                  45

Thr Asp Ser Pro Arg Gly Phe Glu Leu Ser Ser Thr Arg Gln Arg
50                  55                  60

Thr Gln Gly Phe Asn Lys Gln Asp Tyr Asp Leu Met Val Phe Pro Glu
65                  70                  75                  80

Leu Asp Ser Gln Lys Arg Ala Val Asp Ile Asp Val Glu Lys Leu Thr
            85                  90                  95

Gln Ala Glu Leu Glu Lys Ile Leu Leu Asp Asp Asn Phe Glu Thr Arg
        100                 105                 110

Lys Pro Pro Ala Leu Pro Val Thr Pro Val Leu Ser Pro Phe Ser
            115                 120                 125

Thr Gln Leu Tyr Leu Arg Pro Ser Gly Gln Arg Gly Gln Trp Pro Pro
        130                 135                 140

Gly Leu Cys Gly Pro Ser Thr Tyr Thr Leu Pro Ser Thr Tyr Pro Ser
145                 150                 155                 160

Ala Tyr Ser Lys Gln Ala Thr Phe Gln Asn Gly Phe Ser Pro Arg Met
            165                 170                 175

Pro Thr Phe Pro Ser Thr Glu Ser Val Tyr Leu Arg Leu Pro Gly Gln
        180                 185                 190
```

```
Ser Pro Tyr Phe Ser Tyr Pro Leu Thr Pro Ala Thr Pro Phe His Pro
        195                 200                 205

Gln Gly Ser Leu Pro Val Tyr Arg Pro Leu Val Ser Pro Asp Met Ala
        210                 215                 220

Lys Leu Phe Glu Lys Ile Ala Ser Thr Ser Glu Phe Leu Lys Asn Gly
225                 230                 235                 240

Lys Ala Arg Thr Asp Leu Glu Ile Ala Asn Ser Lys Ala Ser Val Cys
                245                 250                 255

Asn Leu Gln Ile Ser Pro Lys Ser Glu Asp Ile Asn Lys Phe Asp Trp
            260                 265                 270

Leu Asp Leu Asp Pro Trp Asp Ala Val Leu Leu Glu Glu Arg Ser Pro
            275                 280                 285

Ser Cys His Leu Glu Arg
        290

<210> SEQ ID NO 9
<211> LENGTH: 7
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa can be Asp or Glu

<400> SEQUENCE: 9

Gly Asp Asp Leu Arg Gly Xaa
1               5

<210> SEQ ID NO 10
<211> LENGTH: 8
<212> TYPE: PRT
<213> ORGANISM: Homo sapiens

<400> SEQUENCE: 10

Phe His Ile Asp Phe Gly His Phe
1               5

<210> SEQ ID NO 11
<211> LENGTH: 6
<212> TYPE: PRT
<213> ORGANISM: Homo sapiens

<400> SEQUENCE: 11

Pro Pro Leu Pro Pro Arg
1               5
```